US010022323B2

(12) United States Patent
Green

(10) Patent No.: US 10,022,323 B2
(45) Date of Patent: Jul. 17, 2018

(54) USE OF STEARATE IN AN INHALABLE FORMULATION

(71) Applicant: VECTURA LIMITED, Wiltshire (GB)

(72) Inventor: Matthew Green, Wiltshire (GB)

(73) Assignee: VECTURA LIMITED, Wiltshire (GB)

( * ) Notice: Subject to any disclaimer, the term of this patent is extended or adjusted under 35 U.S.C. 154(b) by 0 days.

(21) Appl. No.: 14/779,382

(22) PCT Filed: Mar. 28, 2014

(86) PCT No.: PCT/GB2014/051003
§ 371 (c)(1),
(2) Date: Sep. 23, 2015

(87) PCT Pub. No.: WO2014/155134
PCT Pub. Date: Oct. 2, 2014

(65) Prior Publication Data

US 2016/0045435 A1 Feb. 18, 2016

(30) Foreign Application Priority Data

Mar. 28, 2013 (GB) .................................. 1305825.0

(51) Int. Cl.
*A61K 9/00* (2006.01)
*A61K 31/56* (2006.01)
*A61K 47/12* (2006.01)

(52) U.S. Cl.
CPC ............ *A61K 9/0075* (2013.01); *A61K 31/56* (2013.01); *A61K 47/12* (2013.01)

(58) Field of Classification Search
CPC ....... A61K 31/56; A61K 47/12; A61K 9/0075
See application file for complete search history.

(56) References Cited

U.S. PATENT DOCUMENTS

2003/0185764 A1 10/2003 Staniforth et al.
2007/0065373 A1* 3/2007 Morton ................ A61K 9/0073 424/46
2007/0212422 A1* 9/2007 Keller .................. A61K 9/0075 424/498
2009/0209502 A1* 8/2009 Haeberlin ............ A61K 9/0075 514/171
2015/0136130 A1* 5/2015 DeHaan ............... A61K 9/0075 128/203.15

FOREIGN PATENT DOCUMENTS

| | | |
|---|---|---|
| CA | 2347856 | 5/2000 |
| GB | 2434098 | 7/2007 |
| WO | 1987005213 | 9/1987 |
| WO | 2000053158 | 9/2000 |
| WO | 2008000482 | 1/2003 |
| WO | 2005046636 | 5/2005 |
| WO | 2005105043 | 5/2005 |
| WO | 2005089717 | 9/2005 |
| WO | 2006124556 | 11/2006 |
| WO | 2009056851 | 5/2009 |
| WO | 2011073002 | 6/2011 |

OTHER PUBLICATIONS

Magnesium Stearate (Technical Data Sheet; http://www.rockwellnutrition.com/assets/images/docs/magnesiumstearate-techincaldatasheet.pdf, revision date 2005).*
Phadke et al, Drug Development and Industrial Pharmacy, 1991, vol. 17, pp. 901-906.*
Qi Zhou et al., "Effect of Surface Coating with Magnesium Stearate via Mechanical Dry Powder Coating Approach on the Aerosol Performance of Micronized Drug Powders from Dry Powder Inhalers." AAPS Pharmscitech, vol. 14, No. 1, Nov. 30, 2012, pp. 38-44, XP55128906.
International Search Report and Written Opinion of PCT/GB14/51003 dated Jul. 17, 2014.
United Kingdom Search Report in GB1305825.0 dated May 28, 2013.

* cited by examiner

*Primary Examiner* — Mark V Stevens
(74) *Attorney, Agent, or Firm* — Matthew S. Gibson; Ryan P. Cox; Reed Smith LLP

(57) ABSTRACT

The present invention concerns a method for making an inhaled pharmaceutical composition with improved powder handling properties comprising a stearate, a method of preparing such a composition, and the use of such a stearate in a composition when dispensed into a receptacle for use in a dry powder inhaler receptacle.

5 Claims, 11 Drawing Sheets

USE OF STEARATE IN AN INHALABLE FORMULATION

RELATED APPLICATIONS

Figure 1:
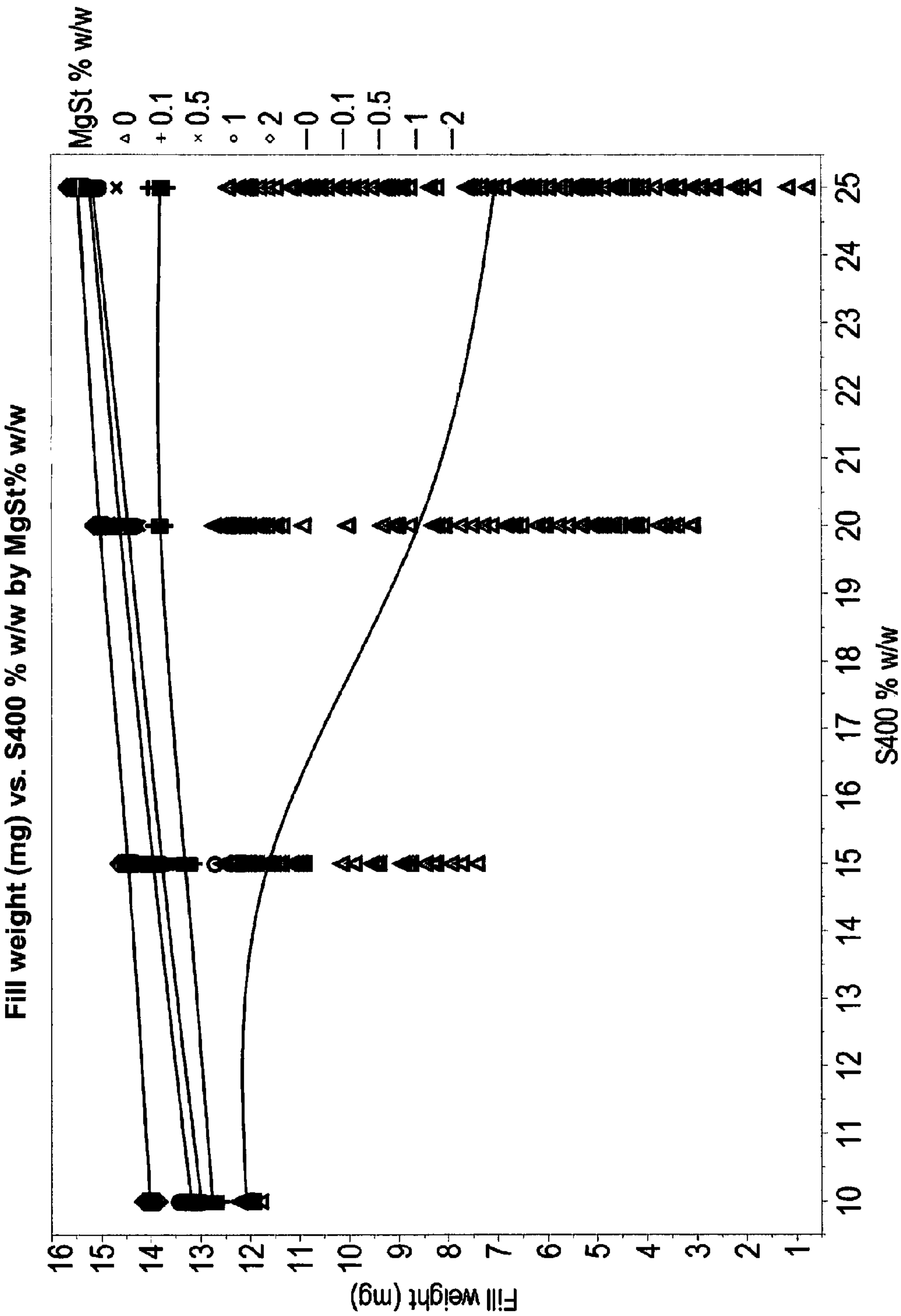

This application is a United States national stage of International Application No. PCT/GB2014/051003, filed Mar. 28, 2014, which was published as International Publication No. WO 2014/155134 A1, and which claims benefit of United Kingdom Application No. 1305825.0 filed, Mar. 28, 2013, the entire contents of which are hereby expressly incorporated herein by reference thereto.

A process is disclosed for preparing a formulation to be administered as dry powder for inhalation suitable for effective delivery of an active ingredient into the lower respiratory tract of a patient. In particular, a process is disclosed for preparing a pharmaceutical composition suitable for inhalation, the formulation having improved filling and handling properties.

BACKGROUND AND PRIOR ART

The efficient dispersal of an active pharmaceutical ingredient is of utmost importance in the field of respiratory medicine. In this field, it is generally desirable to employ therapeutic particles with a size (i.e. geometric diameter) in the range of 1 to 10 μm or an aerodynamic diameter of 1-5 μm in order to be delivered to the lower respiratory tract. Particles above these sizes tend to impact in the regions of the upper airways and are removed by the mucocilliary escalator.

Pulmonary drug delivery, therefore, must overcome the technical challenges of working with fine particles but still operate within the constraints dictated by human anatomy.

To facilitate delivery of cohesive powders a number of solutions have been provided in the art.

Inhaler Devices

Firstly, inhalation devices have been developed for assisting with the delivery of cohesive micronised medicament to the lungs of patients. When a patient actuates a DPI device it produce an air stream, the flow of air produced by the patient's inspiratory manoeuvre lifts the powder out of the inhaler ("Fluidisation") and causes the separation of, inter alia, the drug from carrier ("De-agglomeration").

Dry powder inhalers can be divided into two basic types:

i) single dose inhalers, for the administration of pre-subdivided single doses of the active compound from a pre-metered dosage means such as a capsule or single blister tab;

ii) multidose dry powder inhalers (MDPIs), either with pre-subdivided single doses or pre-loaded with quantities of active ingredient where the drug is stored in a reservoir or blister pack/strip); each dose is created by a metering unit either within the inhaler or within the filling line prior to assembly.

On the basis of the required inspiratory flow rates (l/min) which in turn are strictly depending on their design and mechanical features, DPIs are divided in:

i) low-resistance devices (>90 l/min);

ii) medium-resistance devices (about 60 l/min);

iii) high-resistance devices (about 30 l/min).

The reported flow rates refer to the pressure drop of 4 KPa (Kilopascal) in accordance to the European Pharmacopoeia (EurPh).

For powder inhalers which release the medicament from pre-dosed units, e.g. capsules or blister packs, the same restriction applies for the low-friction operation of the filling apparatus for these unit doses. This low-friction operation is greatly improved with free flowing powder is used, for example by using large carrier particles.

Large Carrier Particles

Numerous approaches have been adopted to manipulate DPI particulate interactions. A further approach to improve the efficiency of most DPI formulations employs carrier particles as a means to overcome powder handling problems. The majority have focused on the physical properties of the carrier, specifically modifying the shape, size, or rugosity of the carrier. Other approaches have focused on producing uniform respirable drug particles by spray drying or supercritical fluid precipitation.

Lactose is the most common carrier used and can constitute more than 99% by weight of a DPI formulation. Lactose carrier particles are traditionally used as a flow aid and they assist with carrying the dose of the active into the lungs. The chemical and physical properties of lactose play an important role in DPI formulations. The selection of the specific grade of lactose is based on the inhaler device, the filling process and the required API release profile. Critically, DPI formulations need to be homogeneous however this is not the only parameter requiring consideration. The adhesion between carrier and drug particle should not be too strong because the drug will not be able to release from the lactose particle during inhalation. Likewise, it should not be so weak that the carrier separates from the carrier during routine powder handling. Furthermore, the drug should always be released from the carrier in the same way. One of the important parameters for the formulation is the particle size of the lactose.

Carrier particles or excipients, such as lactose, for inhaled therapeutic preparations also include significantly larger diameter particles (e.g. 50 to 300 μm) that typically do not penetrate into the respiratory tract to the same degree as the active ingredient.

The most common approach for describing formulations with multiple components (i.e. drug and carrier) is to use laser diffraction analysis. Machines such as the Malvern Mastersizser report results as sections namely the $D_{10}$, $D_{50}$, and $D_{90}$ values based on a volume distribution. The $D_{50}$, the median, is defined as the diameter (in microns) where half of the particle population, by volume, lies below this value. Similarly, the $D_{90}$ is the value wherein 90 percent of the particle distribution, by volume, lies below the stated $D_{90}$ value, and the $D_{10}$ is the value below which to percent of the particle population resides on a volume basis.

The lactose particle size and distribution will also, in many instances, significantly influence pharmaceutical and biological properties, such as, for example, bioavailability. For example, it is well known that coarse lactose in crystalline form has a good flow rate and good physical stability whereas fine lactose powder, such as that produced by conventional fine grinding or milling, generally lacks good flow properties. Lactose prepared by conventional spray drying either lacks desired flow properties or contains too many large sized lactose crystals.

It is well known that one particular drawback associated with conventional means of producing pharmaceutical grade lactose relates to undesirable variations in particle size, morphology and distribution. Such production methods are particularly problematic in that they often lead to excessive and undesirable variations in the fine particle mass ("FPM") of the delivered pharmaceutical active.

Lactose morphology is believed to be another important parameter to control, and it is believed that the degree of surface roughness can influence the interaction between the lactose particle and excipient and as such is now often measured as part of the lactose selection criteria.

In general, it is preferable to use smaller particle sizes for the lactose or a blend of coarse and fine particles lactose because reduction in mean particle size of the lactose has been shown to increase the aerosolisation of various drugs but this smaller size selection is marred with poor flow properties. Therefore until now the routine approach has been simply to use as few fines particles as possible.

Small Particles

Fine particles are, by their nature, cohesive, and whilst simply blending the large carrier particles, additive particles and fine excipient particles together will result in occupation of the high-energy sites on the carrier particles by additive particles, the distribution of the additive particles over these sites will be determined by the amount of energy that is used in the processing step.

One explanation for this observation is that the fine lactose particles occupy areas of high energy on the carrier surface, such as the clefts. With these high energy sites occupied by the fine lactose particles, the drug particles will then preferentially adhere to the lower adhesion sites and consequently the drug will be more easily released. A further benefit of lactose fines is the surface area increases substantially and the potential payload of each carrier also increases.

Fine particles ("Fines") are characterized as particles with a $D_{10}$ below 5 μm, $D_{50}$ below 15 μm and $D_{90}$ below 32 μm as determined by laser diffraction particle size analysis, for example a Spraytec with Inhalation Cell, Malvern Instruments, Malvern, UK. A balance, however, needs to be struck between desirable API detachment and premature detachment due to poor API adherence to the carrier. Whilst the presence of high lactose fines may increase the aerosol performance of a formulation, this comes at the cost of poor powder handling e.g. in conveying and filing processes.

Fine particles tend to be increasingly thermodynamically unstable as their surface area to volume ratio increases, which provides an increasing surface free energy with this decreasing particle size, and consequently increases the tendency of particles to agglomerate. The process of filling from hoppers, may result in the agglomeration of fine particles and adherence of such particles to the walls of the hoppers. This is a problem that results in the fine particles leaving the hopper as large, stable agglomerates, or being unable to leave the hopper and remaining adhered to the interior of the hopper, or even clogging or blocking the hopper. Poor flow from powder hoppers can adversely affect manufacturing operations. The uncertainty on the extent stable agglomerates formation of the particles between each dispension of the filler, and also between different hoppers and different batches of particles, leads to poor dose reproducibility. Furthermore, the formation of agglomerates means that the MMAD of the active particles can be vastly different with agglomerates of the active particles, on occasion, not reaching the required part of the lung.

As particles decrease in size, they become lighter resulting in a transition away from gravitational forces towards interparticulate forces becoming the predominate force. Conversely, as particles increase in size, they become heavier resulting in a transition away from interparticulate towards gravitational forces becoming the predominate force. Smaller particles, therefore, become overwhelmed by the forces of cohesion and adhesion which is why they adhere to one another and form agglomerates or aggregates. The likelihood of cohesion increases with decreasing particle size; particles smaller than 100 μm experience an element of cohesion. This degree of cohension increases with decreasing size.

Micronisation of the active drug is essential for deposition into the lower lungs during inhalation. As a general rule, however, the finer particles become, the stronger the forces of cohesion and/or adhesion between these particles. Strong cohesion/adhesion forces hinder the handling of the powder during the manufacturing process especially pouring and filling of powders. Moreover micronisation or the presence of micronized particles reduces the ability of the formulation to pour or flow freely under gravity ("flowability").

The effect of non-lactose fine excipients on FPD or FPF performance of ternary formulations has also been investigated. Fines of erythritol, glucose, mannitol, polyethylene glycol 6000, sorbitol and trehalose have all been found to increase either the FPD or FPF of a variety of drugs when added. Fines of different materials have produced varying increases in formulation performance compared to each other and to lactose fines, with lactose fines producing poorer, equal and better performance in various studies.

Lactose Fines

The beneficial aerosol effects of fines on an inhaled formulation have been demonstrated through the use of pre-treatment steps in which pre-existing (intrinsic) fine particles were removed from coarse lactose carrier by either air-jet sieving or air washing lactose held on a sieve. The removal of lactose fines was found to decrease the aerosol performance of formulations containing a variety of different drugs, which were blended by different techniques and aerosolised from different inhalers. Such results are in accordance with numerous studies which, when using various grades of carrier material, different inhalers and different drug found that those containing the highest proportion of intrinsic fines gave the greatest aerosol performance (Jones & Prices, 2006).

Consequently, the majority of research in this area has focused on the addition of lactose fines to blends of coarse lactose (typically a 63-90 μm size fraction) and drug. The fine lactose typically used had a volume median diameter (VMD) of 4-7 μm and the proportion added was typically in the range 1.5 to 10%, but proportions as high as 95% have been investigated (Jones & Prices, 2006). Fine lactose in an amount as high as 95% (w/w) leads to highly cohesive formulations.

In addition to pacifying active sites, the addition of fine additive particles may also lead to the formation of fine lactose agglomerates. These lactose agglomerate particles can remain adhered to the coarse carrier lactose during processing and handling and may dramatically reduce the inspirational energy requirements in entrainment and de-aggregation of the drug particles following aerosolisation.

Despite the beneficial aerosol performance imparted by lactose fines, the addition of fines to a formulation has been found to increase device drug retention, the effect has been attributed to either the decreased flowability of powders containing a higher proportion of fine particles. The increased adhesiveness of fine particles is thought to reduce flowability of the entire powder blend in formulations containing fines contents above 10% by weight of the entire formulation. Consequently, despite the beneficial aerosol improvement, there has been a reluctance to use a fines content above 5% by weight of the entire formulation because of the poor powder flow properties of such formulations. This is because lactose fines can increase the occurrence of powder bridging in an inhaled formulation. Powder bridging is the process whereby particles in a powder bed get stuck and jam against one another creating semi-permanent structures in the powder bed. Significant time and resource is required to identify, locate and disrupt these powder bridges before powder filling can resume. Sometimes these semi-permanent structures can break apart just prior to filling into a DPI. The powder surrounding these powder bridges is often not homogeneous resulting in atypical formulation (high or low API content) entering the blisters, capsules, reservoirs of the filling line.

WO 2011 067212 discloses a fine lactose fraction. The 'fine' lactose fraction is defined as the fraction of lactose having a particle size of less than 7 μm, such as less than 6 μm, for example less than 5 μm. The particle size of the 'fine' lactose fraction may be less than 4.5 μm. The fine lactose fraction, if present, may comprise 2 to 10% by weight of the total lactose component, such as 3 to 6% by weight fine lactose, for example 4.5% by weight fine lactose.

WO 1995 011666 describes a process for modifying the surface properties of the carrier particles by dislodging any asperities in the form of small grains without substantially changing the size of the particles. Said preliminary handling of the carrier causes the micronised drug particles to be subjected to weaker interparticle adhesion forces.

EP 0 663 815 describes the addition of finer particles (<10 μm) to coarser carrier particles (>20 μm) for controlling and optimising the amount of delivered drug during the aerosolisation phase.

Lactose fines are not the only component available for manipulating the high energy sites on carrier particles and they may be used in concert with other components.

Additives (FCAs)

Co-processing of carrier particles with low surface energy materials is a further alternative for increasing the aerosolisation efficiencies of dry powder inhaler formulations.

The primary role of these low surface energy materials is to modify the interfacial properties of the carrier particles to decrease drug-carrier adhesion. Also known as Force Control Agents ("FCA") these low surface energy materials include amino acids, phospholipids or fatty acid derivatives such as stearates, particularly magnesium stearate.

Magnesium stearate continues to be used as a tableting aide because of the stearate's glidant properties. Magnesium stearate has also been used to improve aerosol performance (Vectura), to improve resistance to moisture ingress into a formulation (Skyepharma) and to improve resistance to active degradation (Chiesi) by preventing contact with moisture.

Magnesium stearate's use in inhalable formulations leads to a general improvement in the fine particle fraction. This improvement in the inhalable fine particle fraction through the use of magnesium stearate enhances the dosing efficiency to the patient of the dry powder formulations administered by pulmonary inhalation due to an improvement of powder flowability from the dosing receptacle to the patient.

WO 2011 067212 discloses a pharmaceutical grade magnesium stearate, sourced from Peter Greven, complying with the requirements of Ph.Eur/USNF may be used as supplied with a mass median particle size of 8 to 12 μm.

WO 2011 067212 discloses magnesium stearate in a composition in an amount of about 0.2 to 2%, e.g. 0.6 to 2% or 0.5 to 1.75%, e.g. 0.6%, 0.75%, 1%, 1.25% or 1.5% w/w, based on the total weight of the composition. The magnesium stearate will typically have a particle size in the range 1 to 50 μm, and more particularly 1-20 μm, e.g. 1-10 μm. Commercial sources of magnesium stearate include Peter Greven, Covidien/Mallinckodt and FACI.

WO 87/05213 describes a carrier, comprising a conglomerate of a solid water-soluble carrier and a lubricant, preferably magnesium stearate, for improving the technological properties of the powder in such a way as to remedy to the reproducibility problems encountered after the repeated use of a high resistance inhaler device. This teaching focuses exclusively on the ability of magnesium stearate to lubricate the inhaler components.

WO 1996 23485 discloses carrier particles which are mixed with an anti-adherent or anti-friction material consisting of one or more compounds selected from amino acids (preferably leucine); phospholipids or surfactants; the amount of additive and the process of mixing are preferably chosen in such a way as to not give rise to a coating. It is stated that the presence of a discontinuous covering as opposed to a "coating" is an important and advantageous feature. The carrier particles blended with the additive are preferably subjected to the process disclosed in WO 1995 011666.

WO 2000 028979 describes the use of small amounts of magnesium stearate for improving stability to humidity of dry powder formulations for inhalation.

WO 2000 033789 describes an excipient powder for inhalable drugs comprising a coarse first fraction, a fine second fraction, and a ternary agent which may be leucine.

Kassem (London University Thesis 1990) discloses the use of relatively high amount of magnesium stearate (1.5%) for increasing the 'respirable' fraction. However, the reported amount is too great and reduces the mechanical stability of the mixture before use.

Glidants

The role of the tabletting glidant is to improve the flowability of the powder. This is especially important during high speed tableting production. The requirement of adequate powder flow necessitates the use of a glidant to the powder before tableting. Traditionally, talc (1-2% by weight) has been used as a glidant in tablet formulations. The most commonly used tableting glidant is colloidal silica (about 0.2% by weight) which has very small particles that adhere to the surfaces of the other ingredients and improve flow by reducing interparticulate friction.

Magnesium stearate, normally used as a tableting lubricant, can also promote powder flow of the tableting powder at low concentrations (<1% by weight). Concentrations above 1% by weight tend to adversely affect powder flow performance.

Lubricants

The function of the tableting lubricant is to ensure that tablet formation and ejection can occur with low friction between the solid and the die wall. High friction during tableting can cause a series of problems, including inadequate tablet quality and may even stop production. Lubricants are thus included in almost all tablet formulations.

Tableting lubrication is achieved by either fluid lubrication or boundary lubrication. In fluid lubrication a layer of fluid (e.g. liquid paraffin) is located between the particles and die wall and thus reduces the friction.

Boundary lubrication is a surface phenomenon because the sliding surfaces are separated by a thin film of lubricant. The nature of the solid surfaces will therefore affect friction. All substances that can affect interaction between sliding surfaces can be described as boundary lubricants and in the case of tableting, they are fine particulate solids.

A number of mechanisms have been discussed for these boundary lubricants. The most effective tableting tablet boundary lubricant is magnesium stearate because of its properties. The stearic acid salts, including magnesium stearate, are normally used at low concentrations (<1% by weight) in tablet manufacture. Besides reducing friction, lubricants may cause undesirable changes in the properties of the tablet. The presence of a lubricant in a powder is thought to interfere in a deleterious way with the bonding between the particles during compaction, and thus reduce tablet strength. Similarly, lubricants cause undesirable changes in inhaled formulations, especially with respect to reducing the desired adherence of the drug to the carrier particle. These negative effects are strongly related to the amount of lubricant present, and a minimum amount is normally used in a formulation, i.e. concentrations of 1% or below. In addition, the way in which the lubricant is mixed with the other ingredients should also be considered. The sequence, total mixing time and the mixing intensity are also important criteria.

Antiadherent

An antiadherent reduces the adhesion between the powder and the punch faces thereby preventing particles sticking to the tableting punch. Sticking or picking is the phenomenon whereby powders are prone to adhere to the punch. This problem is associated with the moisture content of the powder; higher moisture levels aggravate the problem. The occurrence is also aggravated if the punches are engraved or embossed. Many lubricants, such as magnesium stearate, have also antiadherent properties. However, other substances with limited ability to reduce friction can also act as antiadherents, such as talc and starch.

Agglomerations

A further method of improving the flowing properties of cohesive powders is to agglomerate, in a controlled manner, the micronised particles to form spheres of relatively high density and compactness. The process is termed spheronisation while the particles formed are called pellets. The active ingredient is mixed with a plurality of fine particles of one or more excipients; the resulting product is called a soft pellet.

Generally, flow of compositions comprising fine carrier particles is poor unless they are pelletised (e.g. AstraZeneca's product OXIS (registered trademark). However pelletisation has its own disadvantages including being difficult to perform and produces variable Fine Particle Fractions ("FPF").

The flow properties of the formulation can also be improved by controlled agglomeration of the powder. WO 2004 0117918 discloses a method of preparing a dry powder inhalation composition comprising a pharmaceutically acceptable particulate carrier, a first particulate inhalant medicament and a second particulate inhalant medicament. This application places particular importance in ensuring that any aggregates of the micronized active are broken up and the active ingredient was evenly distributed over the lactose carrier.

U.S. Pat. No. 5,518,998 discloses a therapeutic preparation comprising active compounds and a substance which enhances the absorption of the active in the lower respiratory tract, the preparation is in the form of a agglomerated dry powder suitable for inhalation.

GB 1,569,911 discloses the use of a binder to agglomerate a drug into soft pellets, which is extruded through a sieve to create agglomerates. The formation of soft pellets allows carrier particles to be omitted from the composition. U.S. Pat. No. 4,161,516 also discloses the formation of soft drug pellets to improve powder flow. U.S. Pat. No. 6,371,171 discloses spheronised agglomerates that are able to withstand processing and packaging but de-agglomerate into primary particles during inhalation.

EP 441740 discloses a process and apparatus for agglomerating and metering non-flowable powders preferably constituted of micronised formoterol fumarate and fine particles of lactose (soft pellets). Furthermore several methods of the prior art were generally addressed at improving the flowability of powders for inhalation and/or reducing the adhesion between the drug particles and the carrier particles.

GB 1 242 211, GB 1 381 872 and GB 1 571 629 disclose pharmaceutical powders for the inhalation in which the micronised drug (0.01-10 μm) is respectively mixed with carrier particles of sizes 30 to 80 μm, 800 to 150 μm, and less than 400 μm wherein at least 50% by weight of which is above 30 μm.

The prior art discloses several approaches for improving the flowability properties and the respiratory performances of low strength active ingredients. WO 1998 031353 claims a dry powder composition comprising formoterol and a carrier substance, both of which are in finely divided form wherein the formulation has a poured bulk density of from 0.28 to 0.38 g/ml. Said formulation is in the form of soft pellet and does not contain any additive.

Whilst the matter of improved aerosol performance appears has been adequately addressed by industry. There is still, however, a need for inhalable powders having improved dispersion of the API whilst maintaining superior handling and powder flow characteristics.

Poorly Flowing Powders

In multidose DPIs, cohesive/adhesive particulates impair the loading of the powder from a chamber, thereby creating handling and metering problems.

Poor flowability is also detrimental to the respirable fraction of the delivered dose because the active particles are unable to leave the inhaler. The active particles in a poor flowing powder are either adhered to the interior of the inhaler and/or they leave the inhaler as large agglomerates. Agglomerated particles generally cannot reach the bronchiolar and alveolar sites of the lungs because they are too large and impact in the oralpharyngeal cavity or upper airways. The extent of particulate agglomeration between each actuation of the inhaler and also between inhalers and different batches of particles, leads to poor dose reproducibility making these products unsuitable for patient use.

In this regard, it is well known that the interparticulate forces may be too high and prevent the separation of the micronised drug particles from the surface of the coarse carrier during inhalation. The surface of the carrier particles is, indeed, not smooth but has asperities and clefts, which are high energy sites on which the active particles are preferably attracted to and adhere more strongly.

In consideration of all problems and disadvantages associated with respect to the use of fine lactose, it would be highly advantageous to provide a formulation capable of delivering active ingredients using a DPI device that has excellent flowability.

The Carr index is used in pharmaceutics as a powder flow indicator. A Carr index greater than 25 is considered to be an indication of poorly flowing powder, and below 15, of acceptable flowability.

The Carr index is related to the Hausner ratio, another indication of flowability.

Packaging Lines

The efficiency and profitability of an inhaled product depends on the type of pack and the material selected for the chosen production line. For example, the filling speed for an inhaled formulation will depend on its characteristics: the dosing size, flowability, the propensity of the formulation to segregate, as well as the receptacle into which the powder will be dispensed. For a non-fragile easy-flowing powder, filling speeds for capsules are normally less than 300 000 doses per hour, with 3000 doses per minute for a blister strip (assuming 600 doses per strip and 50 strips per minute) and approximately 3000 doses per minute for a blister pack. Choosing a poorly flowing powder irrespective of the receptacle used could reduce the filling speed to well below these values, severely impacting on the commercial success.

Tablets and inhaled formulations require the ability to be confined into a predetermined space i.e. the filling machine. Tableting, however, requires that the dosage form remain intact and compact following pressing and dispensing into the receptacle. Inhalation, in contrast, presents a completely different technical challenge in that the dosage form is required to withstand a small amount of compaction to assist dispensing of the powder plug from the filling apparatus into the receptacle. Following dispensing into a receptacle this plug must then disintegrate otherwise the powder is not presented in an inhalable form. This dosage form elasticity required by inhaled formulations presents a significant challenge not yet solved in the art, especially when higher fines contents are used.

Acceptable aerosol performance is a crucial parameter for an inhaled formulations and a parameter that is routinely focused on by formulators. However, a formulation that does not readily and reproducible fill into a receptacle does not constitute commercially viable product.

In none of aforementioned documents have the features of the invention been disclosed nor do any of them contemplate the problem or contribute or to the solution of the problem according to the invention.

All the attempts at obtaining stable powder formulations with low strength active ingredients endowed with good flowability and high fine particle fraction according to the teaching of the prior art were unsuccessful as demonstrated by either the prior art or the control examples reported below. In particular, the prior art reports that the proposed solutions for a technical problem (i.e. improving dispersion of the drug particles) was detrimental to other parameters (e.g. improving flowability, mechanical stability) or vice versa.

SUMMARY OF THE INVENTION

The formulation of the invention shows excellent powder flow properties and physical stability combined with good performances in terms of fine particle fraction of more than 15%, more than 20%, more than 30%, more than 40% or preferably more than 50%.

It has been found that, unlike formulations containing conventional carriers with fine particle contents of above 10% which tend to have poor flow properties, the formulations according to an embodiment of the invention have excellent flow properties even with a fines content (that is contents of active particles and fine excipient particles) of up to 40%, preferably up to 50%, preferably up to 60%, preferably up to 70% by weight of the total formulation.

The fines content of the active and fine excipient material can be determined by laser diffraction particle size analysis, for example a Spraytec with Inhalation Cell, Malvern Instruments, Malvern, UK. Fine particles ("Fines") are characterized as particles with a $D_{10}$ below 5 μm, $D_{50}$ below 15 μm and $D_{90}$ below 32 μm as determined by laser diffraction particle size analysis, elucidation of what percentage of the fine fraction is contributed by the excipient, active or additive is not required. The total amount of fines is of primary concern not the constituent parts in this fine fraction. Using this methodology, the fine material may be easily determined in a formulation containing larger carrier particles.

In one embodiment the active is a micronised active.

The phrase "originally exhibited" means the same powder without either a stearate, or without magnesium stearate, or without calcium stearate or without sodium stearate, as the statement or claim so requires.

In one aspect the use of a stearate for improving the powder flow properties of an inhaled formulation is disclosed, wherein the inhaled formulation comprises greater than 10% (w/w) fines content wherein the powder flow property is improved as compared with the powder flow originally exhibited. The improved powder flow characteristics make the powder more amenable for use in an automated filling apparatus as demonstrated by a reduction in the variation of the dosing range of a dispensed inhalable formulation.

In one aspect the use of a stearate for improving the powder flow properties of an inhaled formulation is disclosed, wherein the inhaled formulation comprises greater than 10% (w/w) fines content wherein the powder flow property is improved as compared with the powder flow originally exhibited. The improved powder flow characteristics make the powder more amenable for use in an automated filling apparatus as demonstrated by an improvement in the accuracy of the dosing of the dispensed formulation of the inhalable formulation.

In one aspect the use of a stearate for improving the powder flow properties of an inhaled formulation is disclosed, wherein the inhaled formulation comprises greater than 10% (w/w) fines content wherein the powder flow property is improved as compared with the powder flow originally exhibited. The improved powder flow characteristics make the powder more amenable for use in an automated filling apparatus as demonstrated by an improvement in the precision of the dosing of the dispensed formulation of the inhalable formulation.

In one aspect the use of a stearate for improving the powder flow properties of an inhaled formulation is disclosed, wherein the inhaled formulation comprises greater than 10% (w/w) fines content wherein the powder flow property is improved as compared with the powder flow originally exhibited, wherein the stearate is selected from magnesium stearate, calcium stearate and/or sodium stearate. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation comprising greater than 10% (w/w) fines content is disclosed wherein the powder flow property is improved as compared with the powder flow originally exhibited. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content and wherein the powder flow property is improved as compared with the powder flow originally exhibited wherein the magnesium stearate is present in an amount of from 0.01% to 50% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 45% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 40% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 30% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 20% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 10% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.01% to 5% by weight of the formulation. The improved powder flow characteristics make the powder more amenable for use in an automated filling apparatus as demonstrated by a reduction in the variation of the dosing range of a dispensed inhalable formulation.

In one aspect the use of magnesium stearate for improving the powder flow properties of an inhaled formulation is disclosed, wherein the formulation comprises greater than 10% (w/w) fines content wherein the powder flow property is improved as compared with the powder flow originally exhibited wherein the magnesium stearate is present in an amount of from 0.1% to 2% by weight of the formulation. The improved powder flow characteristics make the powder more amenable for use in an automated filling apparatus as demonstrated by a reduction in the variation of the dosing range of a dispensed inhalable formulation.

In one aspect a method for improving the powder flow characteristics of a pharmaceutical formulation making the powder more amenable for use in an automated filling apparatus is disclosed, as demonstrated by a reduction in the variation of the dosing range of the dispensed formulation. The method comprising the addition of magnesium stearate to the pharmaceutical formulation. The pharmaceutical formulation comprising greater than 10% (w/w) fines content.

In one aspect a method for improving the powder flow characteristics of an inhaled pharmaceutical formulation making the powder more amenable for use in an automated filling apparatus is disclosed, as demonstrated by a reduction in the variation of the dosing range of the dispensed inhalable formulation. The method comprising the addition of magnesium stearate to the pharmaceutical formulation. The inhaled pharmaceutical formulation comprising greater than 10% (w/w) fines content.

In one aspect a method of processing an inhaled pharmaceutical formulation, the method comprising addition of magnesium stearate to the pharmaceutical formulation is disclosed, thereby improving the powder flow characteristics making the powder more amenable for use in an automated filling apparatus as demonstrated by a reduction in the variation of the dosing range of a dispensed inhalable formulation.

In one aspect a method for improving the powder flow characteristics of a pharmaceutical formulation making the powder more amenable for use in an automated filling apparatus is disclosed, as demonstrated by an improvement in the accuracy of the dosing of the dispensed formulation. The method comprising the addition of magnesium stearate in the pharmaceutical formulation. The pharmaceutical formulation comprising greater than 10% (w/w) fines content.

In one aspect a method for improving the powder flow characteristics of an inhaled pharmaceutical formulation making the powder more amenable for use in an automated filling apparatus is disclosed, as demonstrated by an improvement in the accuracy of the dosing of the dispensed inhalable formulation. The method comprising the addition of magnesium stearate in the pharmaceutical formulation. The inhaled pharmaceutical formulation comprising greater than 10% (w/w) fines content.

In one aspect a method of processing an inhaled pharmaceutical formulation, the method comprising addition of magnesium stearate to the pharmaceutical formulation thereby improving the powder flow characteristics making the powder more amenable for use in an automated filling apparatus is disclosed, as demonstrated by an improvement in the accuracy of the dosing of a dispensed inhalable formulation.

In one aspect a method for improving the powder flow characteristics of a pharmaceutical formulation is disclosed by making the powder more amenable for use in an automated filling apparatus as demonstrated by an improvement in the precision of the dosing of the dispensed formulation. The method comprising the addition of magnesium stearate in the pharmaceutical formulation. The pharmaceutical formulation comprising greater than 10% (w/w) fines content.

In one aspect a method for improving the powder flow characteristics of an inhaled pharmaceutical formulation is disclosed by making the powder more amenable for use in an automated filling apparatus as demonstrated by an improvement in the precision of the dosing of the dispensed inhalable formulation. The method comprising the addition of magnesium stearate in the pharmaceutical formulation. The inhaled pharmaceutical formulation comprising greater than 10% (w/w) fines content.

In one aspect a method of processing an inhaled pharmaceutical formulation is disclosed, the method comprising the addition of magnesium stearate to the pharmaceutical formulation thereby improving the powder flow characteristics making the powder more amenable for use in an automated filling apparatus as demonstrated by an improvement in the precision of the dosing of a dispensed inhalable formulation.

In one aspect a method for improving the powder flow characteristics of a pharmaceutical formulation is disclosed, the method making the powder more amenable for use in an automated filling apparatus as demonstrated by a reduction in the variation of the dosing range of the dispensed formulation, and demonstrated by an improvement in the accuracy of the dosing of the dispensed formulation and demonstrated by an improvement in the precision of the dosing of the dispensed formulation. The method comprising the addition of magnesium stearate in the pharmaceutical formulation. The pharmaceutical formulation comprising greater than 10% (w/w) fines content.

In one aspect a method for improving the powder flow characteristics of an inhaled pharmaceutical formulation making the powder more amenable for use in an automated filling apparatus is disclosed, as demonstrated by a reduction in the variation of the dosing range of the dispensed inhalable formulation, and demonstrated by an improvement in the accuracy of the dosing of the dispensed inhalable formulation and demonstrated by an improvement in the precision of the dosing of the dispensed inhalable formulation. The method comprising the addition of magnesium stearate in the pharmaceutical formulation. The inhaled pharmaceutical formulation comprising greater than 10% (w/w) fines content.

In one aspect a method of processing an inhaled pharmaceutical formulation, the method comprising submitting the inhaled pharmaceutical formulation to compression and shearing forces in the presence of magnesium stearate to improve the powder flow characteristics is disclosed thereby making the powder more amenable to use in an automated filling apparatus as demonstrated by a reduction in the variation of the dosing range of a dispensed inhalable formulation.

In one aspect a method of processing an inhaled pharmaceutical formulation is disclosed, the method comprising submitting the inhaled pharmaceutical formulation to compression and shearing forces in the presence of magnesium stearate thereby improving the powder handling characteristics as demonstrated by a reduction in the variation of the dosing range of the dispensed inhalable formulation, wherein the pharmaceutical formulation has a fines content of greater than 5%, greater than 10%, greater than 15%, greater than 20%, greater than 25%, greater than 30%, greater than 35%, greater than 40%, greater than 45% or greater than 50% by weight of the total dispensed formulation as determined by particle size analysis.

A dispensed formulation is the formulation found within a receptacle.

In one embodiment, the cohesiveness between the particles is adjusted in such a way to give sufficient adhesion force to hold the active particles to the surface of the carrier particles during manufacturing of the dry powder and in the delivery device before use, but also enables the effective and reproducible filling of powder into receptacles to be incorporated into inhalation devices.

In one aspect a pharmaceutical formulation obtainable or obtained using the above method is disclosed.

In one aspect an inhaler device comprising a pharmaceutical formulation obtainable or obtained by the method of the invention, or a pharmaceutical formulation which has been further processed where necessary into a suitable pharmaceutically acceptable form is disclosed.

In one aspect a receptacle, such as a blister, capsule or reservoir, comprising a pharmaceutical formulation, obtainable or obtained by the method of the invention, or an active ingredient which has been further processed where necessary into a suitable pharmaceutically acceptable form is disclosed.

In one aspect a powder inhaler is disclosed having a reservoir (also considered a receptacle along with blisters, capsules, blister packs and blister strips), the finished pharmaceutically preparation is filled into the reservoir in the form of a powder bed. A dose is withdrawn by means of a suitably designed dosage device. Withdrawal takes place either volumetrically or gravimetrically. The accurate dosage of the preparation for most active compounds necessitates dilution with a pharmaceutically inactive excipient in order to obtain a measurable unit amount accurately meeting the dosage demands.

In one aspect a method is disclosed for producing an inhaled pharmaceutical formulation, the method comprising addition of magnesium stearate to the pharmaceutical formulation thereby ameliorating the cohesive effect of fine particles and improving the powder handling performance.

In one aspect a method is disclosed for producing an inhaled pharmaceutical formulation, the method comprising addition of magnesium stearate separately to the formulation's constituent components thereby ameliorating the cohesive effect of fine particles and improving the powder handling performance.

In one aspect a method is disclosed for producing an inhaled pharmaceutical formulation, the method comprising addition of magnesium stearate separately to another constituent components of the formulation before addition of other formulation constituents thereby ameliorating the cohesive effect of fine particles and improving the powder handling performance.

In one aspect the powder compositions produced may preferably have a tapped density of more than 0.1 g/cc, more than 0.2 g/cc, more than 0.3 g/cc, more than 0.4 g/cc, more than 0.5 g/cc, more than 0.6 g/cc or preferably more than 0.7 g/cc.

In one aspect the use of a stearate for improving powder flow and aerosol properties of an inhaled formulation wherein the powder flow and aerosol properties are improved as compared with the powder flow and aerosol properties originally exhibited is disclosed, wherein the stearate is selected from magnesium stearate, calcium stearate and/or sodium stearate and wherein magnesium stearate is especially preferred.

In one aspect the use of a stearate for the amelioration of the cohesive effect of fine particles in an inhaled formulation wherein the powder flow properties are improved over the powder flow originally exhibited is disclosed, wherein the formulation fines content is greater than 10%, greater than 15%, greater than 20% or greater than 25% by weight of the formulation as determined by particle size analysis, wherein the stearate is selected from magnesium stearate, calcium stearate and/or sodium stearate, wherein magnesium stearate is especially preferred.

In one aspect a method of dispensing a predetermined amount of an inhalable formulation from an automated powder filling apparatus, the method comprising storing the inhalable formulation comprising magnesium stearate in an amount of from 0.1 to 2.0% by weight of the formulation in a powder hopper, flowing an amount of inhalable formulation from the hopper into a dosing aperture to create a predetermined amount of inhalable formulation, moving the predetermined amount of inhalable formulation within the dosing aperture from a first position to a second position and releasing the predetermined amount of inhalable formulation from the dosing aperture so as to dispense the predetermined amount of inhalable formulation therein with improved dosing reproducibility, is disclosed.

In one aspect a method of improving the dispensed dosing reproducibility of an inhalable formulation from an automated powder filling apparatus comprising storing the inhalable formulation comprising magnesium stearate in an amount of from 0.1 to 2.0% by weight of the formulation in a powder hopper, flowing an amount of inhalable formulation from the hopper into a dosing aperture to create a predetermined amount of inhalable formulation, moving the predetermined amount of inhalable formulation within the dosing aperture from a first position to a second position and releasing the predetermined amount of inhalable formulation from the dosing aperture so as to dispense the predetermined amount of inhalable formulation, is disclosed.

In one aspect an automated powder filling apparatus, for example, Harro Höfliger's Omnidose automated powder filling apparatus and 3Pi's Dosator volumetric filling apparatus are disclosed in combination with all paragraphs disclosed in the summary of the invention.

Formulation Manufacture

The ability to balance the natural cohesion possessed by API and the cohesion contributed by the remaining formulation constituents is a crucial parameter for working the invention.

In view of the present disclosure, the skilled person will now be able to quickly assess the cohesion exhibited by the active particles and the remaining formulation constituents and produce an inhalable formulation with excellent powder handling characteristics despite an elevated level of fine particles.

The following processes, which are not limiting, are suitable to work the invention.

Milling

The process of milling may also be used to formulate the dry powder compositions according to the present invention. The manufacture of fine particles by milling can be achieved using conventional techniques. In the conventional use of the word, "milling" means the use of any mechanical process which applies sufficient force to the particles of active or excipient or additive material that it is capable of (not necessarily does) breaking coarse particles (for example, particles with a $D_{50}$ greater than 100 μm) down to fine particles (for example, having a $D_{50}$ not more than 50 μm) as determined by laser diffraction particle size analysis, for example a Spraytec with Inhalation Cell, Malvern Instruments, Malvern, UK. In the present invention, the term "milling" also refers to deagglomeration of particles in a formulation, with or without particle size reduction. The particles being milled may be large or fine prior to the milling step. A wide range of milling devices and conditions are suitable for use in the production of the compositions of the inventions. The selection of appropriate milling conditions, for example, intensity of milling and duration, to provide the required degree of force will be within the ability of the skilled person.

The process of milling may also be used to formulate the dry powder compositions according to the present invention. The manufacture of fine particles by milling can be achieved using conventional techniques mentioned below and in the examples.

According to one embodiment of the invention, the active agent is milled with a force control agent and/or with an excipient material which can delay or control the release of the active agent when the active particles of the invention are deposited in the lung. Co-milling or co-micronising particles of active agent and particles of FCA or excipient will result in the FCA or excipient becoming deformed and being smeared over or fused to the surfaces of fine active particles.

According to one embodiment of the invention the resultant composite active particles comprising magnesium stearate have been found to be less cohesive after the milling treatment as determined by tapped density when compared with a sample of the active particles prior to processing with magnesium stearate.

The milling processes preferably apply a sufficient degree of force to break up tightly bound agglomerates of fine or ultra-fine particles, such that effective mixing and effective application of the additive material to the surfaces of those particles is achieved.

The additive material is preferably in the form of a coating on the surfaces of the particles of active material. The coating may be a discontinuous coating. The additive material may be in the form of particles adhering to the surfaces of the particles of active material.

At least some of the composite active particles may be in the form of agglomerates. However, when the composite active particles are included in a pharmaceutical composition, the additive material promotes the dispersal of the composite active particles on administration of that composition to a patient, via actuation of an inhaler. The term composite active particle describes a particle of active material completely covered or partially covered with a separate particle of additive material. The particle of additive material has undergone a process of deformation during the construction of the composite active particle. The term composite active particle does not describe a particle of active abutting a particle of additive; there must be a degree of deformation imparted to the particle of additive material. Composite active particles are typically created when the active particle is harder than the particle of additive material. This may be determined by visual inspection; the active material is either completely covered or partially covered with a separate particle of deformed additive material.

The following specific processes, which are not limiting, are suitable to work the invention.

In one aspect processing of an active alone indicates processing in the absence of other materials that might be suitable for inclusion in a pharmaceutical product. For example, processing is carried out in the absence of an excipient. The invention relates, in one particular aspect, to a method of processing an active ingredient, the method comprising submitting an active ingredient or ingredients alone to compression and shearing forces in the absence of magnesium stearate until processing of the active material is completed before magnesium stearate is combined with the ingredients.

Mechanofusion

Mechanofusion has previously been described as a dry process designed to mechanically fuse a first material onto a second material. It should be noted that the use of the terms “mechanofusion” and “mechanofused” are supposed to be interpreted as a reference to a particular type of milling process, but not a milling process performed in a particular apparatus. The compressive milling processes work according to a different principle to other milling techniques (“comminution techniques”), relying on a particular interaction between an inner element and a vessel wall, and they are based on providing energy by a controlled and substantial compressive force.

The active ingredient is fed into the vessel of a mechanofusion apparatus (such as a Mechano-Fusion system (Hosokawa Micron Ltd)) or the Nobilta (Hosokawa Micron Ltd) or Nanocular (Hosokawa Micron Ltd) apparatus, where it is subject to a centrifugal force and is pressed against the vessel inner wall. The active ingredient is compressed between the fixed clearance of the drum wall and a curved inner element with high relative speed between drum and element. The inner wall and the curved element together form a gap or nip in which the particles are pressed together. As a result, the active ingredient experiences very high shear forces and very strong compressive stresses as they are trapped between the inner drum wall and the inner element (which has a greater curvature than the inner drum wall). The particles are pressed against each other with enough energy to locally increase the temperature and soften, break, to distort, flatten and thereby reduce the amount of amorphous/disordered material in the sample.

Either the outer vessel or the inner element may rotate to provide the relative movement. In an alternate embodiment the outer vessel and the inner element may rotate in opposite directions with respect to each other.

The gap between the outer vessel and the inner element surfaces is relatively small, and is typically less than 10 mm and is preferably less than 5 mm, more preferably less than 3 mm, more preferably less than 2 mm, preferably less than 1 mm or preferably less than 0.5 mm. This gap is fixed, and consequently leads to a better control of the compressive energy than is provided in some other forms of mill such as ball and media mills. Alternatively, a sequential use of rotors with smaller gaps throughout the blending process may be used. Such an approach lends itself to providing control over initial powder processing permitting gentler forces before using rotors with smaller gaps to impart a milling process of greater intensity. A sequential use of different rotor speeds may be used throughout the blending process. Such an approach lends itself to providing control over initial powder processing (i.e. deagglomeration) permitting gentler forces before using higher rotor speeds to impart a milling process of greater intensity.

The speed of rotation may vary between the ranges of 200 to 10,000 rpm throughout processing. Typical processing capacity is between 4000-5000 rpm, which equates to 80% engine capacity.

It is, however, preferable to introduce powder into the processing chambers at slower speeds. Introduction of powder at slower speeds prevents clogging because it is easier to process an already moving powder. A scraper may also be present to break up any caked material building up on the vessel surface. This is particularly advantageous when using fine cohesive starting materials.

The local temperature may be controlled by use of a heating/cooling jacked built into the drum vessel walls.

The above processes suitably apply a high enough degree of force to separate individual particles of active ingredient and to break up tightly bound agglomerates of the active ingredient.

Cyclomix

Another compressive milling process that may be used in the present invention is the Cyclomix method. The Cyclomix comprises a stationary conical vessel with a fast rotating shaft with paddles which move close to the wall. Due to the high rotational speed of the paddles, the active ingredient is propelled towards the wall, and as a result it experiences very high shear forces and compressive stresses between wall and paddle. Such effects are similar to those in mechanofusion as described above and may be sufficient to increase the temperature and soften, to break, distort, and flatten the active ingredient particles.

The device used is preferably capable of exerting a force of greater than 1 N. It will be appreciated by the skilled person, that pressure force that is exerted upon the active will be affected by multiple factors including the force imparted by the rotor on the powder when compressed against the drum wall, the volume of powder within the processing chamber, weight of the powder, density of the powder and the inherent cohesiveness of the powder components which dictate the resistance to flow. In addition to these, the speed, temperature, humidity, amount of powder and type of machine can be varied independently to achieve a suitable form of an active according to the present invention.

Hybridiser®

In another aspect the compressive and shearing forces may be carried out by the Hybridiser® Method. The active ingredient is fed into the Hybridiser. The powder is subjected to ultra-high speed impact, compression and shear as it is impacted by blades on a high speed rotor inside a stator vessel, and is re-circulated within the vessel. Typical speeds of rotation are in the range of 5,000 to 20,000 rpm.

Quadro® Comil®

Comills are capable of reducing solids to particle sizes in the low-micron to submicron range. Traditionally, Comils have been used to deaggolmerate powders, specifically powders which are then subsequently combined into blending apparatuses. The grinding energy is created by rotating paddles/stirrers that rotate within close proximity to the conical sieve of the Comil®. Particles in the powder bed are forced against the sieve of the Comil®, forcing the particles active material over the particles of excipient material before the composite particles are forced through the sieve. The interaction of the particles in the powder bed create a violent sheer and as the particles abrade with one another.

In the past, the Comil® has not been considered attractive for milling active and excipient particles, with controlled compressive processes similar to Mechanical Chemical Bonding (mechanofusion) and cyclomixing being clearly preferred. The interaction between the particles in a Comil® are somewhat uncontrolled and those skilled in the art, therefore, considered it unlikely for this technique to be able to provide the desired deposition of a coating of active material on the surface of the excipient particles because the residency time has been difficult to control. Hence the reason for the preference of this apparatus for use as a sieve rather than use this apparatus to force active particle to adhere to particle of excipient thereby creating composite active particles and/or composite excipient particles.

According to the present invention, the powder components undergo a compressive formulation process. The compressive milling processes works according to a different principle to the convention Comil® milling techniques, relying on a particular interaction between an inner element and a sieve wall, and they are based on providing energy by a controlled and substantial compressive force. The powder is compressed between the fixed clearance of the sieve wall and a curved inner element of the Comil® paddle with high relative speed between sieve and paddle. The sieve and the paddle together form a gap of predetermined width in which the particles are pressed together and the active or additive smeared over the excipient. The difference between this formulation process and the mechanofusion process is the presence of the curved inner sieve. The porosity of the sieve affords the formulation sufficient time for adequate blending before leaving the chamber to be collected. This continuous processing and collection beyond the chamber permits a continuous process unlike the batch-type processes of the mechanofusion system. Furthermore the duration of mixing and resultant size of the particles according to the invention can be modified through the selection of sieve size.

The process works particularly well where one of the materials is generally smaller and/or softer than the other. In one aspect the active is harder than the additive allowing the additive distort and wrap around the active thereby creating a composite active particle. In one aspect the excipient is harder than the additive allowing the additive distort and wrap around the excipient thereby creating a composite excipient particle. When the presence of an additive material is required, an especially desirable aspect of the described process is that additive material becomes deformed in the milling and may be smeared over or fused to the surfaces of the active particles to give a uniform appearance.

In another embodiment, the particles produced using a jet-mill process may subsequently undergo processing in a Comil®. This final Comil® step is thought to "polish" the composite active particles (active and additive) or excipient particles (excipient and additive), further rubbing the additive material onto and around the active or excipient particles. This permits the beneficial properties normally afforded to particles produced by mechanofusion but with the advantages of a continuous manufacturing system.

The surprising effect is that a machine routinely used for sieving particles can now be used to spread active over the surface of the excipient and still dramatically improved the aerosolisation performance of the manufactured formulation.

In one aspect, a process for preparing a dry powder pharmaceutical composition is disclosed comprising the steps of pre-blending formulation components until sufficient homogeneity and cohesion is achieved and then milling said pre-blend in a Quadro® Comil® until the final formulation possesses the desired respirable characteristics suitable for administration by pulmonary inhalation.

Ball Milling

Ball milling is a milling method used in many of the prior art co-milling processes. Centrifugal and planetary ball milling may also be used.

Jet Mills and Co-Jet Milling

Jet mills are capable of reducing solids to particle sizes in the low-micron to submicron range. The grinding energy is created by gas streams from horizontal grinding air nozzles. Particles in the fluidised bed created by the gas streams are accelerated towards the centre of the mill, colliding within. The gas streams and the particles carried in them create a violent turbulence and, as the particles collide with one another, they are pulverized.

High Pressure Homogenisers

High pressure homogenisers involve a fluid containing the particles being forced through a valve at high pressure, producing conditions of high shear and turbulence. Suitable homogenisers include EmulsiFlex high pressure homogenisers which are capable of pressures up to 4000 bar, Niro Soavi high pressure homogenisers (capable of pressures up to 2000 bar) and Microfluidics Microfluidisers (maximum pressure 2750 bar).

TURBULA®

The mixing efficiency of the TURBULA is achieved by the interaction of rotation, translation and inversion of the powder container. The TURBULA is considered to be low-shear blending process. This mixer is traditionally used for homogeneous mixing of powdered substances, specifically those with different specific weights and particle sizes. The mixing container turns in a three-dimensional motion and the product is subjected to an ever-changing, rhythmically pulsing motion. The results meet the highest requirements and are achieved in a minimum of time Diosna Diosna type systems are often used to formulate lactose based formulations and are considered to be high-shear blending processes. In fact the predominant formulation process in Diosna type systems is more active to excipient impaction rather than a shearing and smearing of the active to the excipient.

Product Components

Traditionally, dry powder inhaler ("DPI") devices contain particulate active pharmaceutical ingredient ("API") which is mixed with an excipient powder of larger average particle size ("Carrier Particle") and additive of varying particle size ("Additive") to create a homogenous formulation giving rise to so-called "ordered mixtures". In some cases, the additive may comprise a combination of materials, including fine carrier particles ("Lactose Fines"). These fine carrier particles do not function as traditional carrier but instead moderate the interaction of the active with the larger carrier particles by resting on or around the larger carrier. The larger particle size of the carrier facilitates a flowable powder mixture. Furthermore the homogeneity of the mixture enables metering into consistent doses. Obtaining an accurate and consistent dose is of particular importance when very small quantities of the cohesive drug are required.

API

Respirable particles are generally considered to be those with a particle size distribution wherein $D_{10}\leq6$ μm, $D_{50}\leq7$ μm and $D_{90}\leq10$ μm, particles within this distribution are capable of reaching into the bronchiolar and alveolar regions ("lower lung") where the majority of the absorption takes place. Larger particles with a particle size distribution wherein $D_{10}\geq30$ μm, $D_{50}\geq45$ μm and $D_{90}\geq70$ μm are mostly deposited in the oralpharyngeal cavity so they cannot reach the lower lung. The majority of the particles that are smaller than the respirable range tend to be exhaled.

In particular formulations wherein $D_{90}\geq20$ μm are substantially deposited in the oralpharyngeal cavity so they cannot reliably reach the lower lung and are not considered suitable and safe as an inhalable formulation. Formulations wherein $D_{90}\geq20$ μm are eminently suitable for oral delivery. Formulations comprising for example, $D_{50}\geq10$ μm, might possess a lower range of particles considered an inhalable but these formulations contain a substantial proportion of particles which are not suitable for inhalation making the delivery inconsistent and consequently unsafe from an inhalation perspective.

It is well known that particle impaction in the upper airways of a subject is predicted by the so-called impaction parameter. The impaction parameter is defined as the velocity of the particle multiplied by the square of its aerodynamic diameter. Consequently, the probability associated with delivery of a particle through the upper airways region to the target site of action, is related to the square of its aerodynamic diameter. Therefore, delivery to the lower airways, or the deep lung is dependent on the square of its aerodynamic diameter, and smaller aerosol particles are very much more likely to reach the target site of administration in the user and therefore able to have the desired therapeutic effect.

In one aspect of the invention the active ingredient may be micronised prior to compression and shearing. Micronisation may be by any suitable method. Micronization is the process of reducing the average diameter of particles of a solid material, for example by milling or grinding.

In one aspect the active ingredient is in the form of particles prior to processing.

In one aspect reference to processing of an active ingredient alone herein includes reference to processing of two or more actives alone, unless otherwise clear from the context.

In one aspect of the invention the composition is a dry powder which has a fine particle fraction (<5 μm) of at least 30%, preferably at least 40%, at least 50% or at least 60% when measured at 600 L/min using a New Generation Impactor ("NGI") apparatus delivered from a Monohaler inhalation device.

Metered Dose/Nominal Dose

The metered dose (MD), also known as the Nominal Dose (ND), of a dry powder composition is the total mass of active agent present in the metered form presented by the inhaler device in question i.e. the amount of drug metered in the dosing receptacle or container. For example, the MD might be the mass of active agent present in a capsule for a Cyclohaler™, or in a foil blister in a GyroHaler™ device or powder indentations of the frustoconical dispensing cone of a ClickHaler™.

The MD is different to the amount of drug that is delivered to the patient (i.e. does that leave the inhaler device) which is referred to a Delivered Dose (DD) or Emitted Dose (ED). These terms are used interchangeably herein and they are measured as set out in the current EP monograph for inhalation products.

Emitted Dose

The emitted dose (ED) is the total mass of the active agent emitted from the device following actuation. It does not include the material left on the internal or external surfaces of the device, or in the metering system including, for example, the capsule or blister. The ED is measured by collecting the total emitted mass from the device in an apparatus frequently identified as a dose uniformity sampling apparatus (DUSA), and recovering this by a validated quantitative wet chemical assay (a gravimetric method is possible, but this is less precise).

Fine Particle Dose

The fine particle dose (FPD) is the total mass of active agent which is emitted from the device following actuation which is present in an aerodynamic particle size smaller than a defined limit. This limit is generally taken to be 5 μm if not expressly stated but an alternative limit, such as 3 μm, 2 μm or 1 μm, etc may be used. The FPD is measured using an impactor or impinger, such as a twin stage impinger (TSI), multi-stage impinger (MSI), Andersen Cascade Impactor (ACI) or a Next Generation Impactor (NGI). Each impactor or impinger has a pre-determined aerodynamic particle size collection cut points for each stage known to the person skilled in the art. The FPD value is obtained by interpretation of the stage-by-stage active agent recovery quantified by a validated quantitative wet chemical assay (a gravimetric method is possible, but this is less precise) where either a simple stage cut is used to determine FPD or a more complex mathematical interpolation of the stage-by-stage deposition is used.

Fine Particle Fraction

The fine particle fraction (FPF) is normally defined as the FPD (the dose that is <5 μm) divided by the Emitted Dose (ED) which is the dose that leaves the device. The FPF is expressed as a percentage. Herein, the FPF of ED is referred to as FPF (ED) and is calculated as FPF (ED)=(FPD/ED)×100%.

The fine particle fraction (FPF) may also be defined as the FPD divided by the Metered Dose (MD) which is the dose in the blister or capsule, and expressed as a percentage. Herein, the FPF of MD is referred to as FPF (MD), and may be calculated as FPF (MD)=(FPD/MD)×100%.

Fine Particle Mass

The fine particle mass (FPM) is the weight of medicament within a given dose that reaches the desired size airways to be effective.

Ultrafine Particle Dose

The term "ultrafine particle dose" (UFPD) is used herein to mean the total mass of active material delivered by a device which has a diameter of not more than 3 μm. The term "ultrafine particle fraction" is used herein to mean the percentage of the total amount of active material delivered by a device which has a diameter of not more than 3 μm. The term percent ultrafine particle dose (% UFPD) is used herein to mean the percentage of the total metered dose which is delivered with a diameter of not more than 3 μm (i.e., % UFPD=100×UFPD/total metered dose).

As used herein, the term "pharmaceutically acceptable esters" of active refers to for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butryates, acrylates and ethyl succinates.

Additive Material

In one aspect of the present invention the additive may comprise a metal stearate, or a derivative thereof, for example, sodium stearyl fumarate or sodium stearyl lactylate. Advantageously, it comprises a metal stearate, for example, zinc stearate, magnesium stearate, calcium stearate, sodium stearate or lithium stearate. Preferably, the additive material comprises magnesium stearate, for example vegetable magnesium stearate, or any form of commercially available metal stearate, which may be of vegetable or animal origin and may also contain other fatty acid components such as palmitates or oleates.

In one aspect the additive may include or consist of one or more surface active materials. A surface active material may be a substance capable reducing the surface tension of a liquid in which it is dissolved. Surface active materials may in particular be materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific In one aspect the additive may include cholesterol.

In one aspect the additive may include sodium benzoate, hydrogenated oils which are solid at room temperature, talc, titanium dioxide, aluminium dioxide, silicon dioxide and starch. Also useful as additives are film-forming agents, fatty acids and their derivatives, as well as lipids and lipid-like materials.

In one aspect the additive particles may comprise lactose.

In one aspect the additive particles may comprise composite additive particles comprising lactose fines.

The additive lactose may be added a various stages of the formulation assembly or the additive lactose may be formed as a result of processing of a larger lactose carrier particle. Said processing produces smaller lactose particles that may adhere to the larger carrier particles or combine with different components of the composition.

In one aspect a plurality of different additive materials can be used.

Carrier Particles

According the invention carrier particles may be of any acceptable inert excipient material or combination of materials. For example, carrier particles frequently used in the prior art may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles comprise a polyol. In particular, the carrier particles may be particles of crystalline sugar, for example mannitol, dextrose or lactose. Preferably, the carrier particles are composed of lactose. Suitable examples of such excipient include LactoHale 300 (Friesland Foods Domo), LactoHale 200 (Friesland Foods Domo), LactoHale 100 (Friesland Foods Domo), PrismaLac 40 (Meggle), InhaLac 70 (Meggle).

In one aspect the ratio in which the carrier particles (if present) and active ingredient are mixed will depend on the type of inhaler device used, the type of active particle used and the required dose. In one aspect the carrier particles may be present in an amount of at least 50%, more preferably 70%, advantageously 90% and most preferably 95% (w/w) based on the weight of the formulation.

In accordance with the present invention, the term "lactose" as used herein is to be broadly construed. As an example, lactose is intended to encompass physical, crystalline, amorphous and polymorphic forms of lactose, including, but not limited to, the stereoisomers α-lactose monohydrate and β-anhydrous lactose, as well as α-anhydrous lactose. Combinations of the above may be used.

In one aspect the for example a plurality of milled lactose particles may exist in at least two fractions having an average particle size ($D_{50}$) ranging from about 5-microns as well as a coarse fraction having an average particle size ($D_{50}$) ranging from about 60-250 microns, as measured by Malvern particle sizing.

In one aspect the compositions of the present invention comprise active particles, preferably comprising conditioned active, and carrier particles. The carrier particles may have an average particle size of from about 5 to about 1000 μm, from about 4 to about 40 μm, from about 600 to about 200 μm, or from 150 to about 1000 μm as measured by Malvern particle sizing. Other useful average particle sizes for carrier particles are about 20 to about 30 μm or from about 40 to about 70 μm as measured by Malvern particle sizing. The skilled artisan would have no problems in balancing the cohesion of each API employed with the size of carrier or type of additive.

In one aspect the carrier particles are present in small amount, such as no more than 90%, preferably 80%, more preferably 70%, more preferably 60% more preferably 50% by weight of the total composition. In such "low carrier" compositions, the composition preferably also includes at least small amounts of additive materials, to improve the powder properties and performance.

In one aspect the compositions according to the invention may further include one or more additive materials. The additive material may be in the form of particles which tend to adhere to the surfaces of the active particles, as disclosed in WO 1997 003649.

In one aspect the additive material may be coated onto the surface of carrier particles present in the composition. This additive coating may be in the form of particles of additive material adhering to the surfaces of the carrier particles (by virtue of interparticle forces such as Van der Waals forces), as a result of a blending of the carrier and additive. Alternatively, the additive material may be smeared over and fused to the surfaces of the carrier particles, thereby forming composite particles with a core of inert carrier material and additive material on the surface. For example, such fusion of the additive material to the carrier particles may be achieved by co-milling particles of additive material and carrier particles. In some embodiments, all three components of the powder (active, carrier and additive) are processed together so that the additive becomes attached to or fused to both the carrier particles and the active particles. For the avoidance of doubt, fine particles obtained from the carrier should, for the purpose of this disclosure, be considered as additive material.

In one aspect the formulation or pharmaceutical composition may comprise two or more actives that have been conditioned independently to vary extents and subsequently combined. For example, an active may be combined with pharmaceutically slower acting active to provide a combination which has the benefit of rapid onset of action but also conveying the benefit of low recurrence due to their longer half-life.

In one aspect the compositions according to the present invention are prepared by simply blending particles of conditioned active of a selected appropriate size with particles of other powder components, such as additive and/or carrier particles. The powder components may be preblended by a gentle mixing process, for example in a tumble mixer such as a Turbula®. In such a gentle mixing process, there is generally substantially no reduction in the size of the particles being mixed. In addition, the powder particles do not tend to become fused to one another, but they rather agglomerate as a result of cohesive forces such as Van der Waals forces. Depending on the degree of cohesion between the particles of API, cohesive agglomerates may behave like larger particles. These larger particles are therefore unable to reach the desired site of action with in the pulmonary system resulting on inefficient drug deposition. A benefit of the present invention is the agglomerates are spread over the surface of the excipient resulting in dispersion whereby the particles of API are less likely to adhere to each other. These dispersed particles readily release from the excipient upon actuation of the inhaler device used to dispense the composition.

A number of measures may be taken to ensure that the compositions according to the present invention have good flow and dispersion properties and these are discussed herein. One or more of these measures may be adopted in order to obtain a composition with properties that ensure efficient and reproducible drug delivery to the lung.

In one aspect carrier particles are included to improve the flow and dispersion properties of the compositions of the present invention.

Powder flow problems associated with compositions comprising larger amounts of fine material, such as up to from 5 to 20% by total weight of the formulation. This problem may be overcome by the use of large fissured lactose carrier particles, as discussed in earlier patent applications published as WO 2001 078694, WO 2001 078695 and WO 2001 078696.

In one aspect powder density is increased, even doubled, for example from 0.3 g/cm$^3$ to over 0.5 g/cm$^3$. Other powder characteristics are changed, for example, the angle of repose is reduced and contact angle increased.

Improved powder handling characteristics and dispensed dosing reproducibility means:

(i) an improvement in powder flow as determined by an increase in powder fill weight for the same volume of a dispensed formulation; or (ii) Alternatively, improved powder handling characteristics and dispensed dosing reproducibility means an improvement in powder flow as determined by a decrease in powder fill weight variation of a dispensed formulation. A decrease in powder fill weight variation is observed when the range between the largest and smallest powder fill weights narrows; or (iii) Alternatively, improved powder handling characteristics and dispensed dosing reproducibility means an improvement in powder flow as determined by an increase in powder fill weight accuracy of a dispensed formulation. An increase in powder fill weight accuracy is observed when the degree of closeness of measurements of the powder fill weights more closely match that which is expected for the powder dispensing chamber and the bulk density of the sample powder; or (iv) Alternatively, improved powder handling characteristics and dispensed dosing reproducibility means an improvement in powder flow is determined by an increase in powder fill weight precision of a dispensed formulation. An increase in powder fill weight precision is observed when the repeated dispensed measurements under unchanged conditions i.e. powder dispensing chamber and the bulk density of the sample powder, show more similar results; or (v) Alternatively, improved powder handling characteristics and dispensed dosing reproducibility means an improvement in powder flow is determined by improved dose disaggregation of a dispensed formulation as determined by improved blister weight evacuation.

Improved powder handling characteristics may also mean any combination of properties mentions in paragraphs (i) to (v) above, since these are not mutually exclusive. All these benefits mentioned in paragraphs (i) to (v) above with respect to improving dispensed dosing reproducibility of the inhalable formulation from an automated powder filling apparatus have been surprisingly found attributable by the use of a stearate, and in particular use of magnesium stearate in an inhalable formulation.

Force Control Agents

The compositions according to the present invention may include additive materials that control the cohesion and adhesion of the particles of the powder.

The tendency of fine particles to agglomerate means that the FPF of a given dose can be highly unpredictable and a variable proportion of the fine particles will be administered to the lung. This is observed, for example, in formulations comprising pure drug in fine particle form. Such formulations exhibit poor flow properties and poor FPF.

The additive material or FCA may be in the form of particles which tend to adhere to the surfaces of the active particles, as disclosed in WO 97/03649. Alternatively, it may be coated on the surface of the active particles by, for example a co-milling method as disclosed in WO 02/43701.

Advantageously, the FCA is an anti-friction agent or glidant and will give the powder formulation better flow properties in the inhaler. The materials used in this way may not necessarily be usually referred to as anti-adherents or anti-friction agents, but they will have the effect of decreasing the cohesion between the particles or improving the flow of the powder and they usually lead to better dose reproducibility and higher FPFs.

The reduced tendency of the particles to bond strongly, either to each other or to the device itself, not only reduces powder cohesion and adhesion, but can also promote better flow characteristics. This leads to improvements in the dose reproducibility because it reduces the variation in the amount of powder metered out for each dose and improves the release of the powder from the device. It also increases the likelihood that the active material, which does leave the device, will reach the lower lung of the patient.

In one aspect the FCA comprises a metal stearates such as magnesium stearate, phospholipids, lecithin, colloidal silicon dioxide and sodium stearyl fumarate, and are described more fully in WO 1996 023485, which is hereby incorporated by reference.

The optimum amount of additive material or FCA will depend upon the precise nature of the material used and the manner in which it is incorporated into the composition. In one aspect the the powder advantageously includes not more than 8%, more advantageously not more than 5%, more advantageously not more than 3%, more advantageously not more than 2%, more advantageously not more than 1%, and more advantageously not more than 0.5% FCA by weight of the formulation. In one aspect the powder contains about 1% FCA by weight of the formulation. In other embodiments, the FCA is provided in an amount from about 0.1% to about 10%, and preferably from about 0.5% to 8%, most preferably from about 1% to about 5% by weight of the formulation.

When the FCA is micronised leucine or lecithin, it is preferably provided in an amount from about 0.1% to about 10% by weight of the formulation. Preferably, the FCA comprises from about 3% to about 7%, preferably about 5%, of micronised leucine. Preferably, at least 95% by weight of the micronised leucine has a particle diameter of less than 150 μm, preferably less than 100 μm, and most preferably less than 50 μm as determined by laser diffraction particle size analysis, for example a Spraytec with Inhalation Cell, Malvern Instruments, Malvern, UK.

In one aspect magnesium stearate or sodium stearyl fumarate is used as the FCA, it is preferably provided in an amount from about 0.05% to about 10%, from about 0.15% to about 7%, from about 0.25% to about 6%, or from about 0.5% to about 5% by weight of the formulation. In one aspect, the composition includes an FCA, such as magnesium stearate (up to 10% w/w) or leucine, said FCA being jet-milled with the particles of conditioned active prior to addition to the Comil®.

In one aspect the FCA may comprise or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof, such as glyceryl behenate. Specific examples of such surface active materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the FCA may comprise or consist of cholesterol. Other useful FCAs are film-forming agents, fatty acids and their derivatives, as well as lipids and lipid-like materials. In some embodiments, a plurality of different FCAs can be used.

Advantageously, in the "carrier free" formulations, at least 90% by weight of the particles of the powder have a particle size less than 63 μm, preferably less than 30 μm and more preferably less than to μm. As indicated above, the size of the particles of conditioned active (or its pharmaceutically acceptable salts) in the powder should be within the range of about from 0.1 μm to 5 μm for effective delivery to the lower lung. Where the additive material is in particulate form, it may be advantageous for these additive particles to have a size outside the preferred range for delivery to the lower lung.

Understanding the principles outlined in this disclosure, the skilled artisan would appreciate the parameters that require amendment in order to produce a suitable formulation.

In one aspect the use of magnesium stearate is disclosed in an inhalable formulation to improve dosing consistency when dispensing from high throughput automated dispensers.

In one aspect the use of magnesium stearate in an amount of about 0.05% to about 15%, from about 0.10% to about 7%, from about 0.15% to about 6%, or from about 0.17% to about 5% by weight of the formulation is disclosed to improve dosing speed, dosing precision and/or dosing accuracy of an inhalable formulation when dosing from a high throughput automated dispenser.

In one aspect the presence of magnesium stearate increases the density of the formulation as compared to a formulation without magnesium stearate. The increase in the density may be confirmed by determining the tapped density before and after the addition of magnesium stearate to the formulation.

Without wishing to be bound by theory, the lubricant properties facilitate interparticle slippage allowing the particles to bed down with greater efficiency and thereby occupy a smaller space for an equivalent amount/mass of powder without magnesium stearate. This increased density allows for greater amounts of powder to be dispensed in a predetermined space of the dosing machine.

In one aspect the presence of magnesium stearate moderates the fill weights between formulations of various fines levels. The presence of magnesium stearate minimises the variation in the fill weights between formulations of various fines levels. In other words, a formulation containing 10% fines will have a similar density to a formulation containing 15% fines. Similar densities have the distinct advantage that the powder filling operator avoids the need to change filling equipment, for example powder filling heads, unlike a formulation without magnesium stearate.

In one aspect of the present invention, different formulations batches can be manufactured to have similar/identical densities due to the moderating effect of magnesium stearate. The inclusion of magnesium stearate removes the need to replace filling equipment components between batches because inter-batch variation with respect to formulation density can now be removed.

Delivery Devices

The inhalable compositions in accordance with the present invention are preferably administered via a dry powder inhaler (DPI), but can also be administered via a pressurized metered dose inhaler (pMDI), or even via a nebulised system. Blisters, capsules, reservoir dispensing systems and the like are provided, comprising doses of the compositions according to the invention.

Inhaler devices are provided for dispensing doses of the compositions according to the invention. In one embodiment of the present invention, the inhalable compositions are administered via a dry powder inhaler (DPI).

Dry Powder Inhalers

The compositions according to the present invention may be administered using active or passive DPIs. As it has now been identified how one may tailor a dry powder formulation to the specific type of device used to dispense it, this means that the perceived disadvantages of passive devices where high performance is sought may be overcome.

Preferably, these FPFs are achieved when the composition is dispensed using an active DPI, although such good FPFs may also be achieved using passive DPIs, especially where the device is one as described in the earlier patent application published as WO 2005 037353 and/or the dry powder composition has been formulated specifically for administration by a passive device.

In one embodiment of the invention, the DPI is an active device, in which a source of compressed gas or alternative energy source is used. Examples of suitable active devices include Aspirair™ (Vectura) and the active inhaler device produced by Nektar Therapeutics (as disclosed in U.S. Pat. No. 6,257,233), and the ultrasonic Microdose™ or Oriel™ devices.

In an alternative embodiment, the DPI is a passive device, in which the patient's breath is the only source of gas which provides a motive force in the device. Examples of "passive" dry powder inhaler devices include the Rotahaler™ and Diskhaler™ (GlaxoSmithKline) and the Turbohaler™ (Astra-Draco) and Novolizer™ (Viatris GmbH) and Gyro-Haler™ (Vectura).

The dry powder formulations may be pre-metered and kept in capsules or foil blisters which offer chemical and physical protection whilst not being detrimental to the overall performance. Alternatively, the dry powder formulations may be held in a reservoir-based device and metered on actuation.

Examples of "reservoir-based" inhaler devices include the Clickhaler™ (Innovata) and Duohaler™ (Innovata), and the Turbohaler™ (Astra-Draco). Actuation of such reservoir-based inhaler devices can comprise passive actuation, wherein the patient's breath is the only source of energy which generates a motive force in the device.

Dry powder inhalers can be "passive" devices in which the patient's breath is the only source of gas which provides a motive force in the device. Examples of "passive" dry powder inhaler devices include the Rotahaler and Diskhaler (GlaxoSmithKline), the Monohaler (MIAT), the Gyrohaler (trademark) (Vectura) the Turbohaler (Astra-Draco) and Novolizer (trade mark) (Viatris GmbH). Alternatively, "active" devices may be used, in which a source of compressed gas or alternative energy source is used. Examples of suitable active devices include Aspirair (trade mark)

(Vectura Ltd) and the active inhaler device produced by Nektar Therapeutics (as covered by U.S. Pat. No. 6,257, 233).

It is generally considered that different compositions perform differently when dispensed using passive and active type inhalers. Passive devices create less turbulence within the device and the powder particles are moving more slowly when they leave the device. This leads to some of the metered dose remaining in the device and, depending on the nature of the composition, less deagglomeration upon actuation. However, when the slow moving cloud is inhaled, less deposition in the throat is often observed. In contrast, active devices create more turbulence when they are activated. This results in more of the metered dose being extracted from the blister or capsule and better deagglomeration as the powder is subjected to greater shear forces. However, the particles leave the device moving faster than with passive devices and this can lead to an increase in throat deposition.

Particularly preferred "active" dry powder inhalers are referred to herein as Aspirair® inhalers and are described in more detail in WO 01/00262, WO 02/07805, WO 02/89880 and WO 02/89881, the contents of which are hereby incorporated by reference. It should be appreciated, however, that the compositions of the present invention can be administered with either passive or active inhaler devices.

Other Inhalers

In a yet further embodiment, the compositions are dispensed using a pressurised metered dose inhaler (pMDI), a nebuliser or a soft mist inhaler. Drug doses delivered by pressurised metered dose inhalers tend to be of the order of 1 µg to 3 mg. Examples of suitable devices include pMDIs such as Modulite® (Chiesi), SkyeFine™ and SkyeDry™ (SkyePharma). Nebulisers such as Porta-Neb®, Inquaneb™ (Pari) and Aquilon™, and soft mist inhalers such as eFlow™ (Pari), Aerodose™ (Aerogen), Respimat® Inhaler (Boehringer Ingelheim GmbH), AERx® Inhaler (Aradigm) and Mystic™ (Ventaira Pharmaceuticals, Inc.).

Compositions suitable for use in these devised include solutions and suspensions, both of which may be dispensed using a pressurised metered dose inhaler (pMDI). The pMDI compositions according to the invention can comprise the dry powder composition discussed above, mixed with or dissolved in a liquid propellant.

In one embodiment, the propellant is CFC-12 or an ozone-friendly, non CFC propellant, such as 1,1,1,2-tetrafluoroethane (HFC 134a), 1,1,1,2,3,3,3 heptafluoropropane (HFC-227), HCFC-22 (difluororchloromethane), HFA 152 (difluoroethane and isobutene) or combinations thereof. Such formulations may require the inclusion of a polar surfactant such as polyethylene glycol, diethylene glycol monoethyl ether, polyoxyethylene sorbitan monolaurate, polyoxyethylene sorbitan monooleate, propoxylated polyethylene glycol, and polyoxyethylene lauryl ether for suspending, solubilising, wetting and emulsifying the active agent and/or other components, and for lubricating the valve components of the pMDI.

BRIEF DESCRIPTION OF THE DRAWINGS/FIGURES

FIG. 1 discloses a graphical comparison of the blister fill weights obtained for formulations containing 0, 0.1, 0.5, 1 and 2% (w/w) magnesium stearate and 10, 15, 20 and 25% (w/w) lactose fines (S400) in an Omnidose automated powder filling apparatus. Individual fill weights are represented to illustrate the variation in data. The fill weights for formulations containing magnesium stearate are higher than fill weights for the formulation without magnesium stearate demonstrating the increased density obtainable with magnesium stearate containing formulation. The variation in fill weight data points increases with increasing levels of lactose fines (S400) for the formulations that do not contain magnesium stearate. This fill weight variation is counteracted by the use of magnesium stearate in formulations when used in an amount of 0.1 to 2% (w/w) of the formulation.

Figure 2:
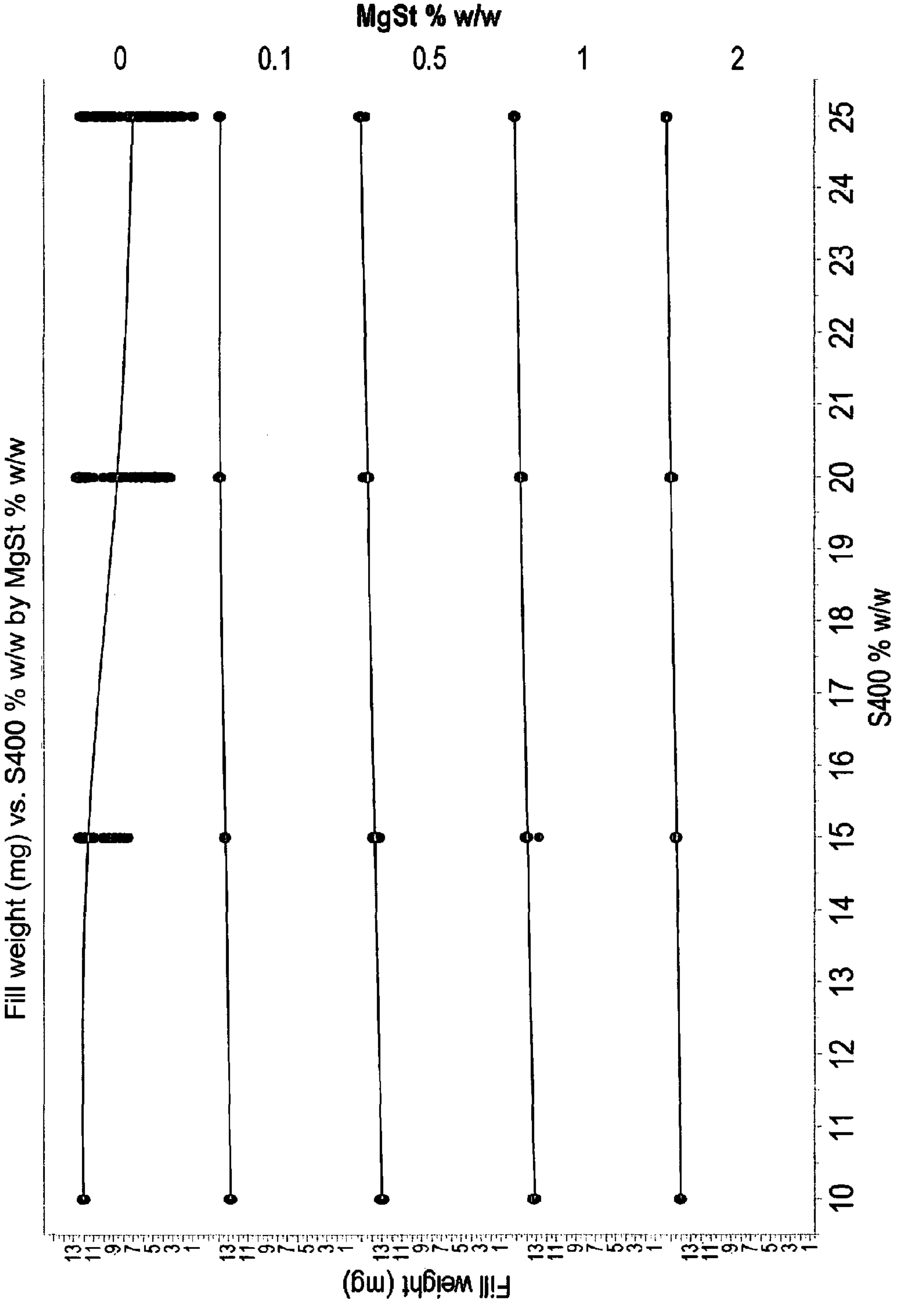

FIG. 2 discloses a separate graphical comparison of the blister fill weights presented in FIG. 1.

Figure 3:
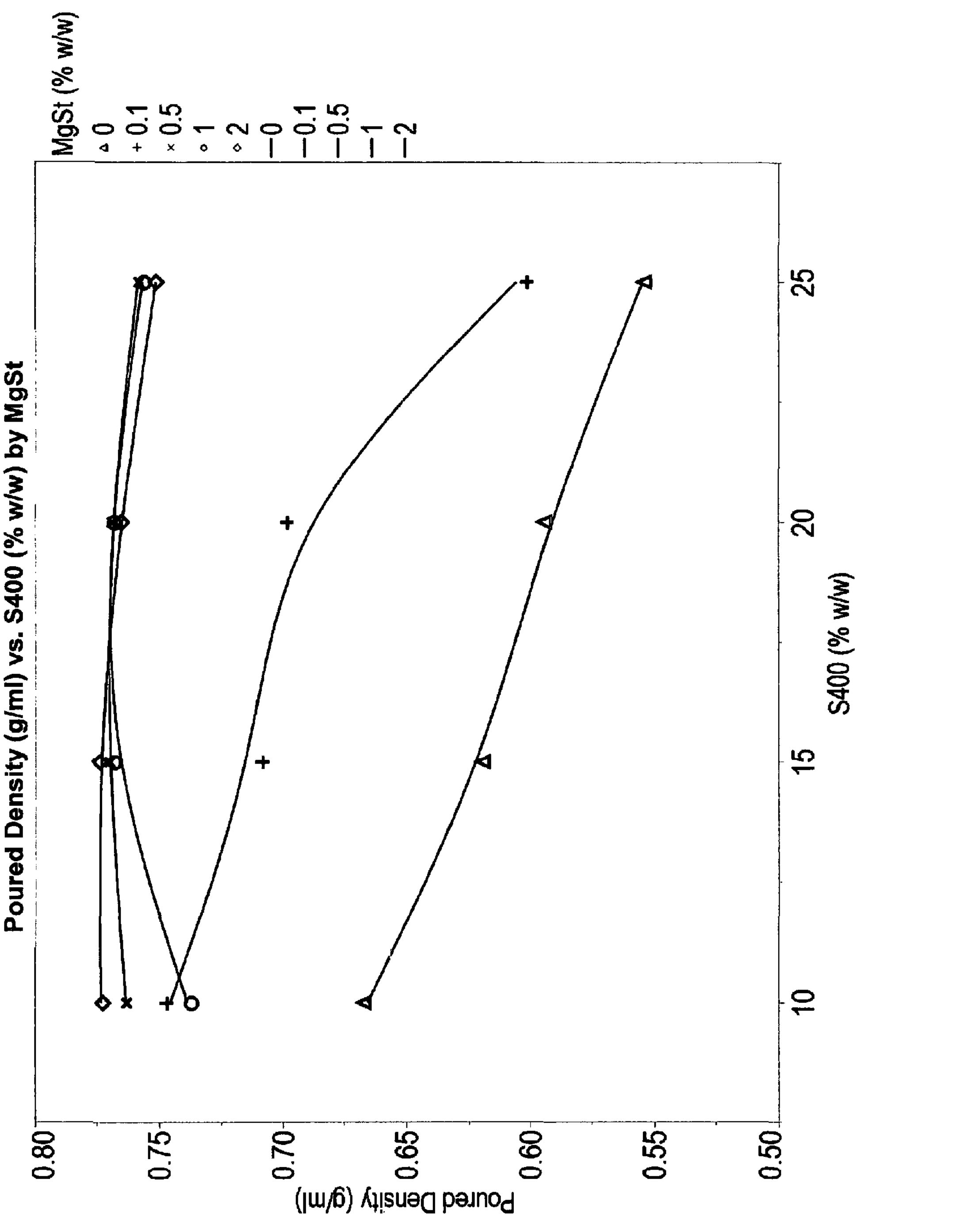

FIG. 3 discloses a graphical comparison of the poured density obtained for formulations containing 0, 0.1, 0.5, 1 and 2% (w/w) magnesium stearate and 10, 15, 20 and 25% (w/w) lactose fines.

Figure 4:
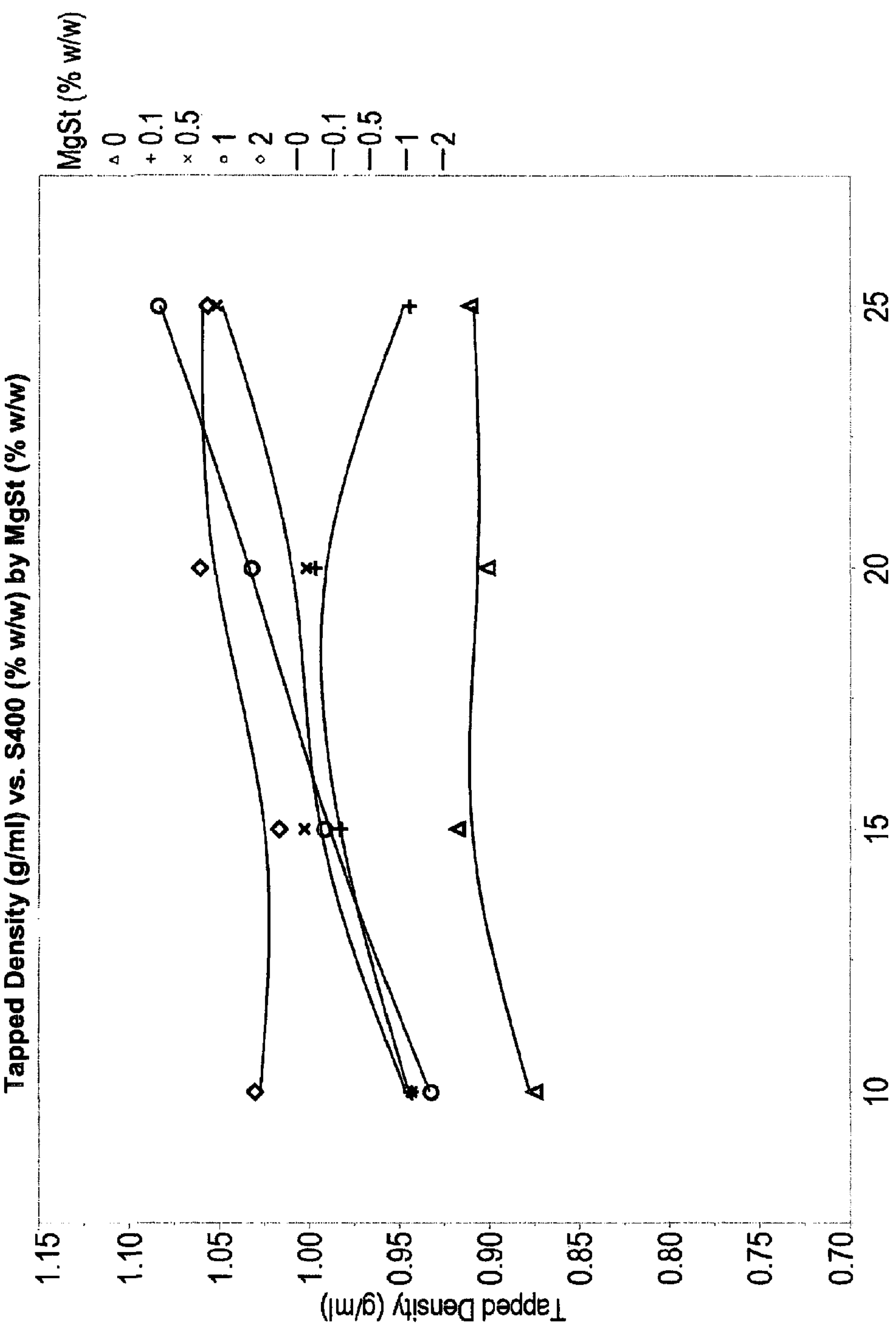

FIG. 4 discloses a graphical comparison of the tapped density obtained for formulations containing 0, 0.1, 0.5, 1 and 2% (w/w) magnesium stearate and 10, 15, 20 and 25% (w/w) lactose fines.

Figure 5:
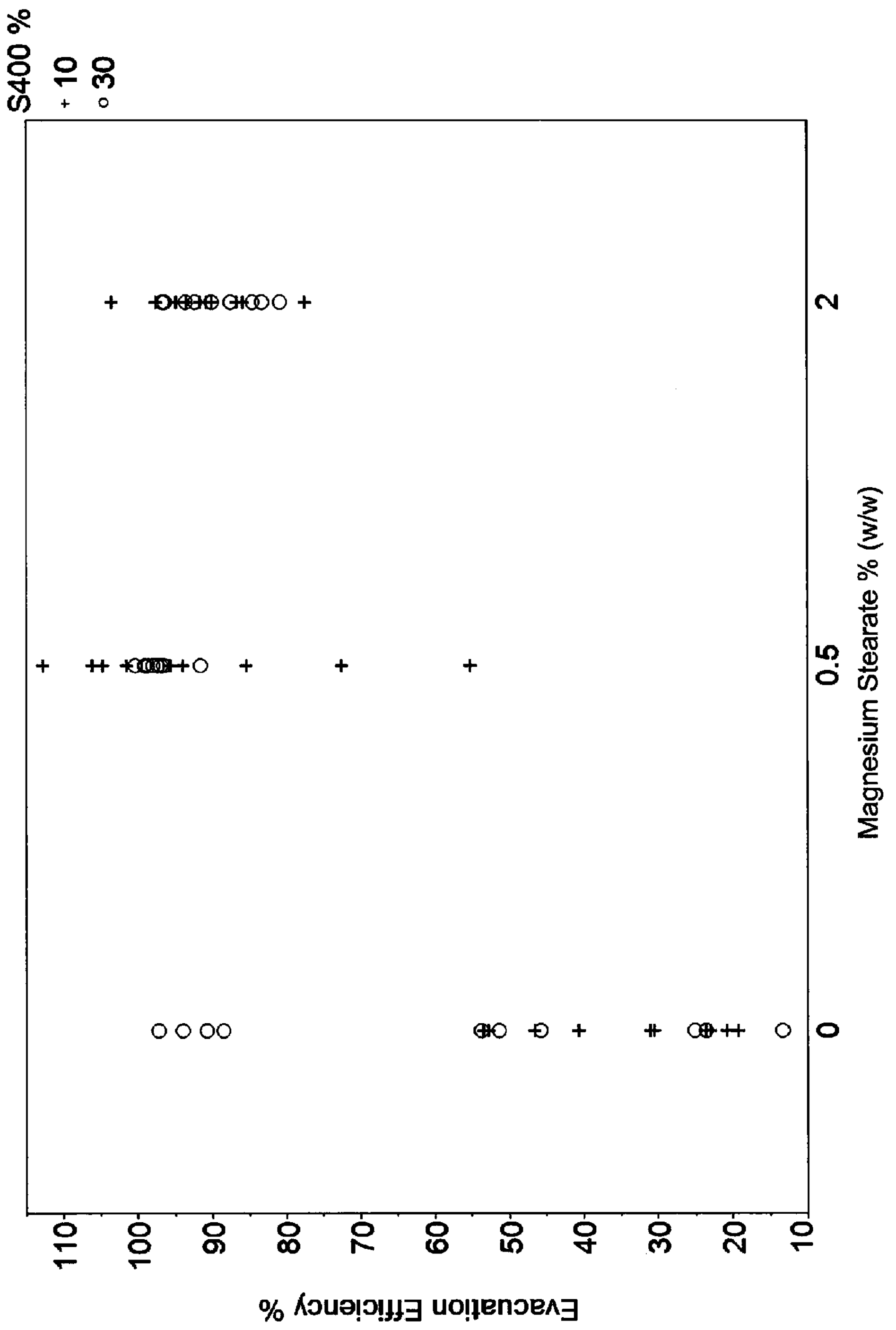

FIG. 5 discloses a plot of magnesium stearate concentration on the x axis against percentage blister evacuation on the y axis. Blue dots indicate 10% (w/w) S400 and red dots indicate 30% (w/w) S400. N=10 at each magnesium stearate level for each concentration of S400. Data points are offset on the x axis to aid visualisation, this is not an indication of minute differences in magnesium stearate concentration.

Figure 6:
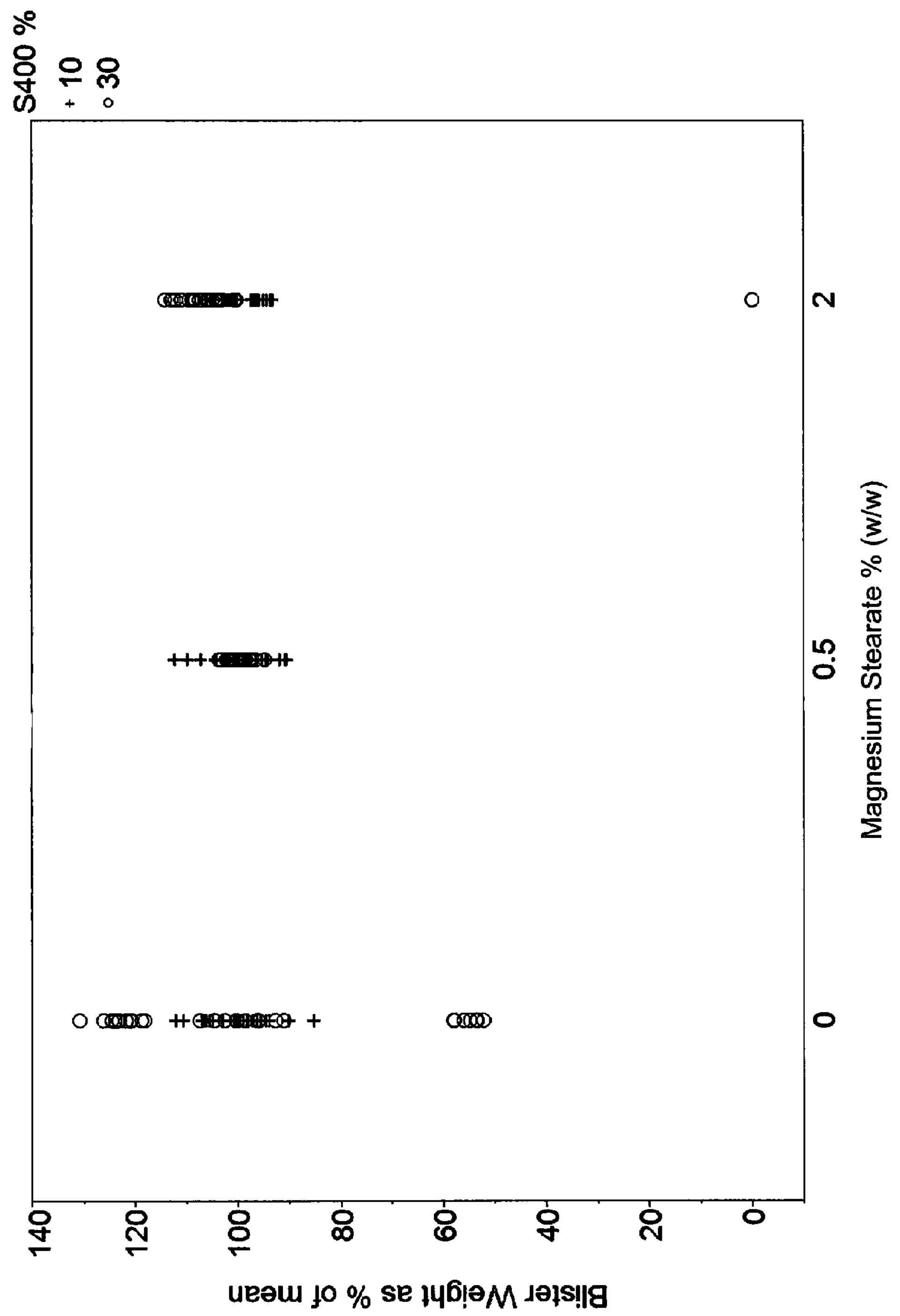

FIG. 6 discloses plot of magnesium stearate concentration on the x axis against blister weight as a percentage of mean blister weight (for each experimental run) on the y axis. Blue dots indicate 10% (w/w) S400 and red dots indicate 30% (w/w) S400. N=30 at each magnesium stearate level for each concentration of S400. Data points are offset on the x axis to aid visualisation, this is not an indication of minute differences in magnesium stearate concentration.

Figure 7:
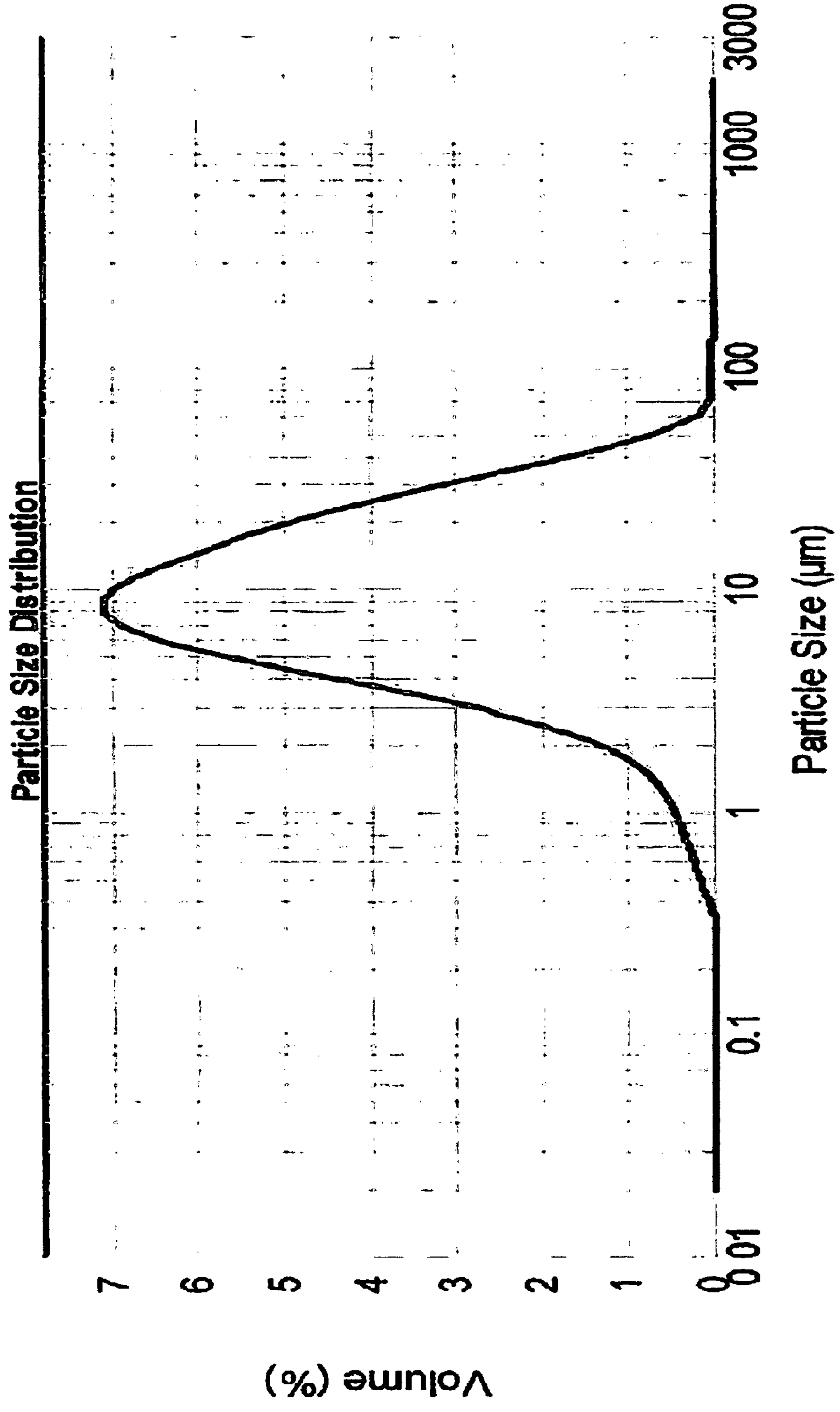

FIG. 7 discloses a Malvern Mastersizer particle size distribution of the magnesium stearate used throughout these experiments as determined by wet analysis measured in Cyclohexane.

Figure 8:
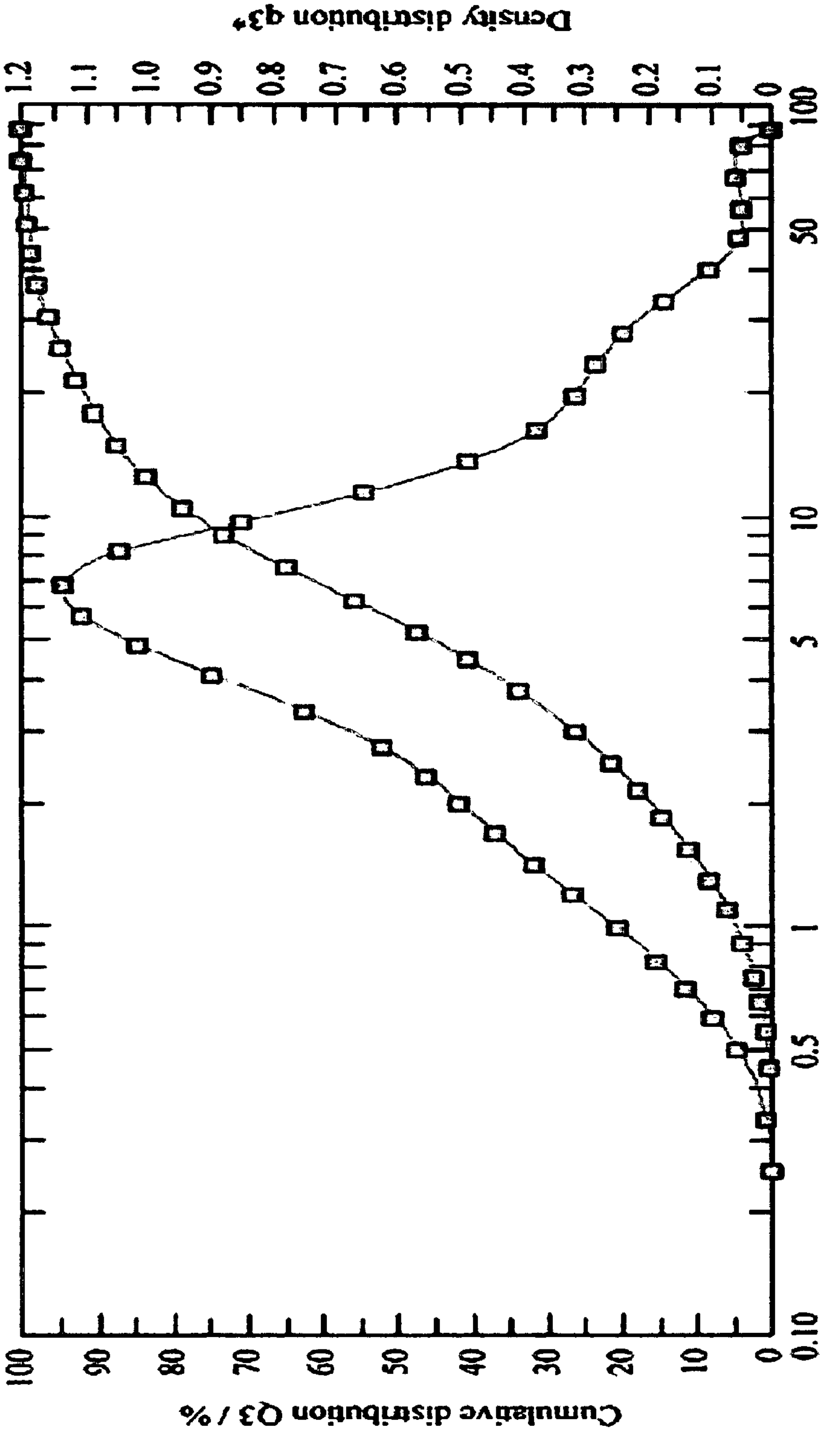

FIG. 8 discloses a Sympatec particle size distribution of magnesium stearate used throughout these experiments as determined by dry analysis. The dry method was performed at a dispersion pressure of 4 bar.

Figure 9:
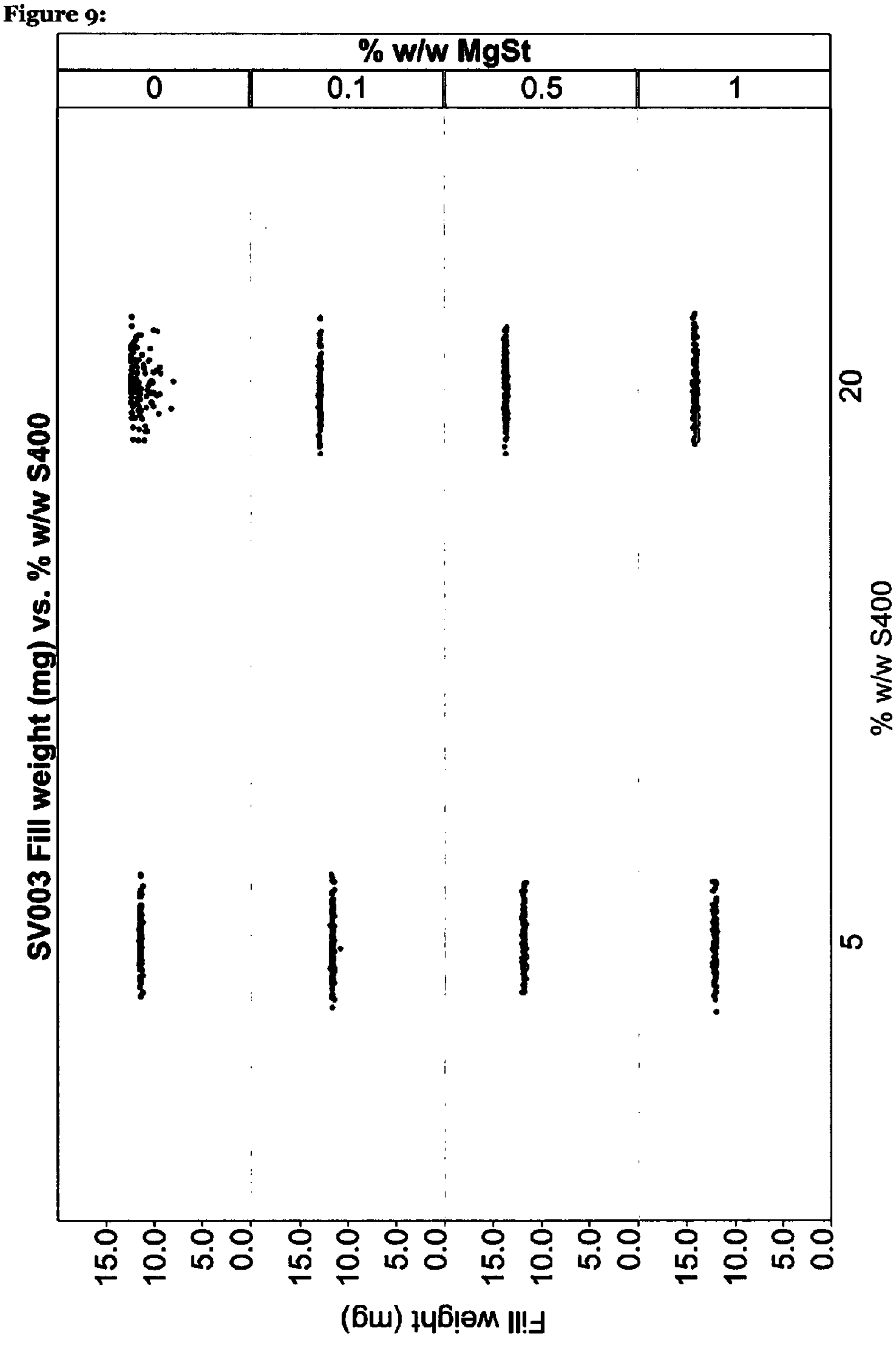

FIG. 9 discloses the individual fill weights obtained for formulations comprising SV003 carrier lactose, with either 5% or 20% (w/w) additional fines (S400), with either 0.0%, 0.1%, 0.5% or 1.0% (w/w) magnesium stearate. The figure shows that SV003, a formulation possessing levels of inherent fines is able to fill reproducibly even when challenged with the addition of 5% (w/w) lactose fines (S400) and 0.8 (w/w) drug (fluticasone propionate). Whereas the same formulation comprising additional of 20% (w/w) lactose fines (S400) and 0.8 (w/w) drug (fluticasone propionate) requires a stearate (magnesium stearate) at 0.1% (w/w) to improve the dosing reproducibility.

Figure 10:
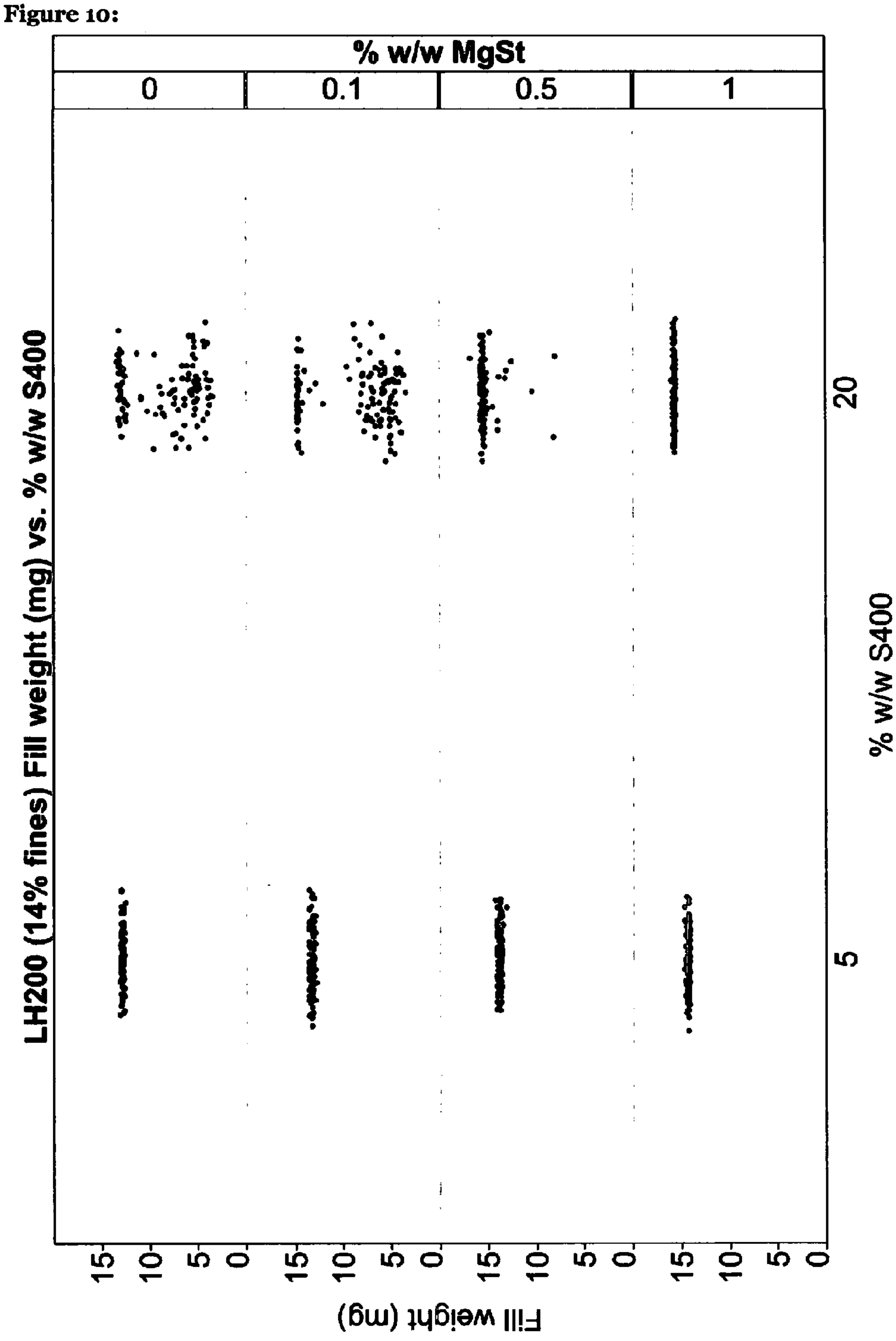

FIG. 10 discloses the individual fill weights obtained for formulations comprising LH200 (with 14% fines) carrier lactose, with either 5% or 20% (w/w) additional fines (S400), with either 0.0%, 0.1%, 0.5% or 1.0% (w/w) magnesium stearate. The figure shows that LH200, a formulation possessing levels of inherent fines is able to fill reproducibly even when challenged with the addition of 5% (w/w) lactose fines (S400) and 0.8 (w/w) drug (fluticasone propionate). Whereas the same formulation comprising additional of 20% (w/w) lactose fines (S400) and 0.8 (w/w) drug (fluticasone propionate) requires a stearate (magnesium stearate) at 0.5% (w/w) to improve the dosing reproducibility and 1.0% (w/w) magnesium stearate produces an acceptable formulation.

Figure 11:
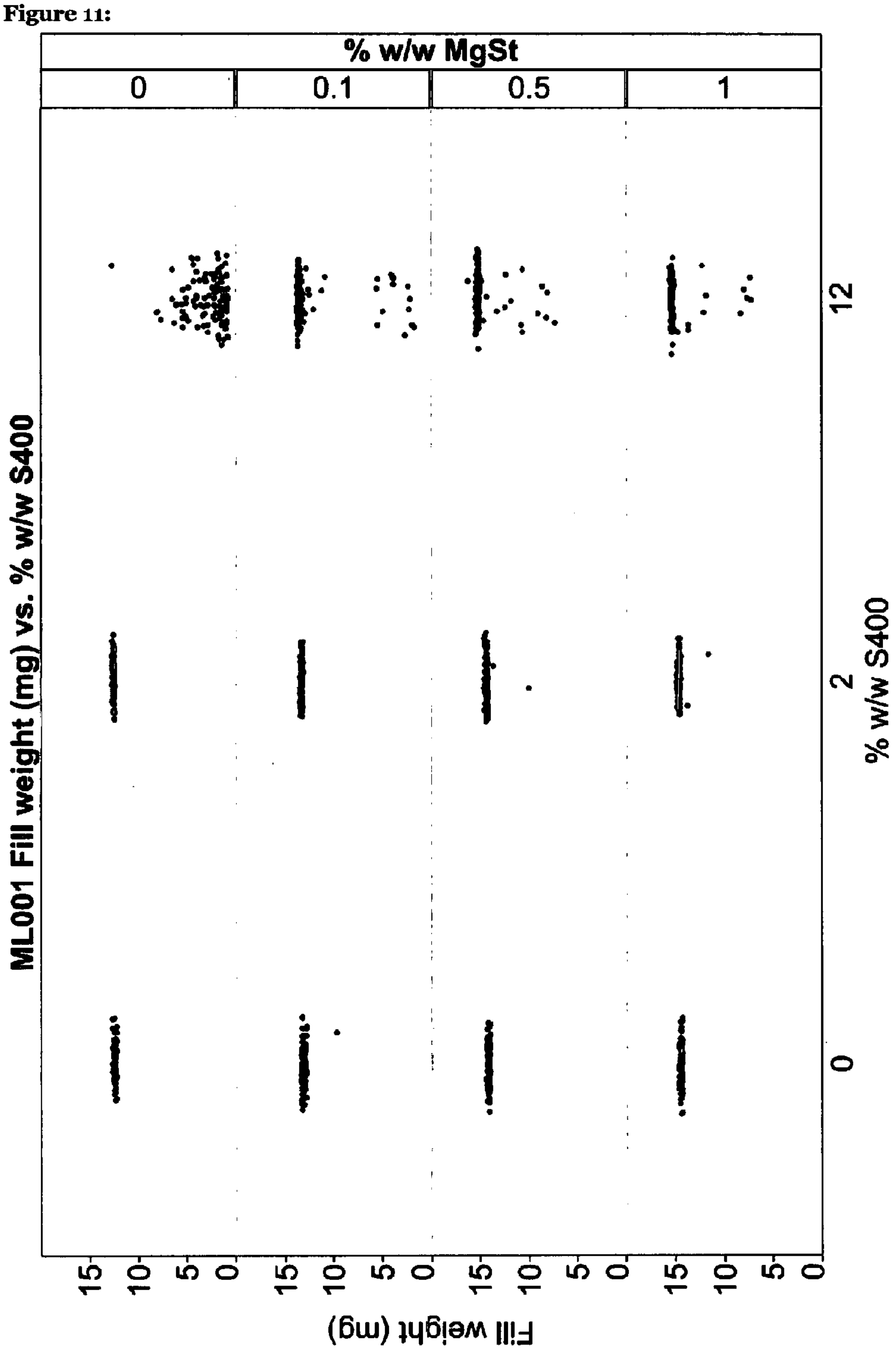

FIG. 11 discloses the individual fill weights obtained for formulations comprising ML001 carrier lactose, with either 0%, 2% or 12% (w/w) additional fines (S400), with either 0.0%, 0.1%, 0.5% or 1.0% (w/w) magnesium stearate. The figure shows that ML001, a formulation possessing levels of inherent fines is able to fill reproducibly even when challenged with the addition of 2% (w/w) lactose fines (S400) and 0.8 (w/w) drug (fluticasone propionate). Whereas the same formulation comprising additional of 12% (w/w) lactose fines (S400) and 0.8 (w/w) drug (fluticasone propionate) requires a stearate (magnesium stearate) at 1.0% (w/w) to improve the dosing reproducibility and produce an acceptable formulation.

EXAMPLES

Measures that may be taken to ensure that the compositions according to the invention have good flow and dispersion properties involve the preparation or processing of the powder particles, and in particular of the active and fine lactose particles. The following examples illustrate the invention.

Example 1

Blending Procedure

Formulations were manufactured to a 300 g scale using the Comil and Diosna Pl/6 in ratios according to Table 1 below:

TABLE 1

Blended Compositions comprising fluticasone propionate (FP), magnesium stearate (MgSt), S400 fine lactose and SV003 Carrier Lactose.

| Formulation Constituents (% w/w) | | | |
|---|---|---|---|
| MgSt | FP | S400 | SV003 |
| 0 | 0.8 | 10 | 89.20 |
| 0 | 0.8 | 15 | 84.20 |
| 0 | 0.8 | 20 | 79.20 |
| 0 | 0.8 | 25 | 74.20 |
| 0.1 | 0.8 | 10 | 89.10 |
| 0.1 | 0.8 | 15 | 84.10 |
| 0.1 | 0.8 | 20 | 79.10 |
| 0.1 | 0.8 | 25 | 74.10 |
| 0.5 | 0.8 | 10 | 88.70 |
| 0.5 | 0.8 | 15 | 83.70 |
| 0.5 | 0.8 | 20 | 78.70 |
| 0.5 | 0.8 | 25 | 73.70 |
| 1 | 0.8 | 10 | 88.20 |
| 1 | 0.8 | 15 | 83.20 |
| 1 | 0.8 | 20 | 78.20 |
| 1 | 0.8 | 25 | 73.20 |
| 2 | 0.8 | 10 | 87.20 |
| 2 | 0.8 | 15 | 82.20 |
| 2 | 0.8 | 20 | 77.20 |
| 2 | 0.8 | 25 | 72.20 |

Fluticasone propionate was sieved using a 500 μm sieve prior to incorporation into each blend.

Half the SV003 was processed in a Comil, after which the magnesium stearate, fluticasone propionate, Sorbolac 40000 and the remaining SV003 were added in sequence. The Comil was operated at 1000 rpm using a 457 μm screen.

The Comiled material was transferred into a 1 liter Diosna bowl and blended at rpm for 7 minutes 48 seconds. The blended material was removed for storage in sealed glass amber jars at ambient laboratory conditions.

Observations

Physical characterisation and comparison to similar blends without magnesium stearate yielded the following observations:

The blends containing magnesium stearate exhibited generally higher bulk density measurements which were largely independent of the change in fine particle content until relatively high concentrations of S400 as demonstrated in FIG. 3. The effect was more pronounced at the 2% w/w magnesium stearate level.

The blends containing magnesium stearate exhibited generally higher tapped density measurements which increased with the increase in fine particle content until relatively high concentrations of S400. This was compared to a general downward trend in tapped density with increased fine particle content for comparable non-magnesium stearate blends as demonstrated in FIG. 4. The effect was more pronounced at the 2% w/w magnesium stearate level.

TABLE 2

Filling results for batches containing 0, 0.1, 0.5, 1 and 2% (w/w) magnesium stearate

| Batch Details | | | | Omnidose Filling Results | | | |
|---|---|---|---|---|---|---|---|
| MgSt (% w/w) | FP (% w/w) | S400 (% w/w) | SV003 (% w/w) | Mean (mg) | Min (mg) | Max (mg) | RSD % |
| 0 | 0.80 | 10 | 89.20 | 12.08 | 11.78 | 12.22 | 0.60 |
| 0 | 0.80 | 15 | 84.20 | 11.64 | 7.43 | 12.56 | 11.18 |
| 0 | 0.80 | 20 | 79.20 | 8.60 | 3.08 | 12.72 | 39.61 |
| 0 | 0.80 | 25 | 74.20 | 7.07 | 0.77 | 12.45 | 46.09 |
| 0.1 | 0.80 | 10 | 89.10 | 12.77 | 12.57 | 12.93 | 0.69 |
| 0.1 | 0.80 | 15 | 84.10 | 13.32 | 13.11 | 13.46 | 0.62 |
| 0.1 | 0.80 | 20 | 79.10 | 13.81 | 13.67 | 13.95 | 0.37 |
| 0.1 | 0.80 | 25 | 74.10 | 13.81 | 13.63 | 14.04 | 0.44 |
| 0.5 | 0.80 | 10 | 88.70 | 13.00 | 12.65 | 13.29 | 1.23 |
| 0.5 | 0.80 | 15 | 83.70 | 13.78 | 13.17 | 14.02 | 1.19 |
| 0.5 | 0.80 | 20 | 78.70 | 14.46 | 14.21 | 14.95 | 0.67 |
| 0.5 | 0.80 | 25 | 73.70 | 15.17 | 14.68 | 15.34 | 0.58 |
| 1.0 | 0.80 | 10 | 88.20 | 13.19 | 12.96 | 13.42 | 0.70 |
| 1.0 | 0.80 | 15 | 83.20 | 13.96 | 12.70 | 14.18 | 1.09 |
| 1.0 | 0.80 | 20 | 78.20 | 14.62 | 14.30 | 14.78 | 0.54 |
| 1.0 | 0.80 | 25 | 73.20 | 15.23 | 15.03 | 15.37 | 0.41 |
| 2.0 | 0.80 | 10 | 87.20 | 14.02 | 13.83 | 14.16 | 0.51 |
| 2.0 | 0.80 | 15 | 82.20 | 14.47 | 14.29 | 14.65 | 0.47 |
| 2.0 | 0.80 | 20 | 77.20 | 15.03 | 14.74 | 15.16 | 0.50 |
| 2.0 | 0.80 | 25 | 72.20 | 15.47 | 15.27 | 15.68 | 0.49 |

TABLE 3

Density results for batches containing 0, 0.1, 0.5, 1 and 2% (w/w) magnesium stearate

| Batch Details | | | | Density Results | | | |
|---|---|---|---|---|---|---|---|
| MgSt (% w/w) | FP (% w/w) | S400 (% w/w) | SV003 (% w/w) | Poured Density (g/ml) | Tapped Density (g/ml) | Hausner Ratio (AU) | Carrs Index (%) |
| 0 | 0.80 | 10 | 89.20 | 0.667 | 0.8747 | 1.3 | 23.8 |
| 0 | 0.80 | 15 | 84.20 | 0.619 | 0.9174 | 1.5 | 32.6 |
| 0 | 0.80 | 20 | 79.20 | 0.594 | 0.9009 | 1.5 | 34.1 |
| 0 | 0.80 | 25 | 74.20 | 0.554 | 0.9103 | 1.6 | 39.1 |
| 0.1 | 0.80 | 10 | 89.10 | 0.747 | 0.9433 | 1.3 | 20.8 |
| 0.1 | 0.80 | 15 | 84.10 | 0.708 | 0.9825 | 1.4 | 27.9 |
| 0.1 | 0.80 | 20 | 79.10 | 0.698 | 0.9966 | 1.4 | 30.0 |
| 0.1 | 0.80 | 25 | 74.10 | 0.601 | 0.9440 | 1.6 | 36.4 |
| 0.5 | 0.80 | 10 | 88.70 | 0.763 | 0.9432 | 1.2 | 19.1 |
| 0.5 | 0.80 | 15 | 83.70 | 0.770 | 1.0027 | 1.3 | 23.3 |
| 0.5 | 0.80 | 20 | 78.70 | 0.769 | 1.0017 | 1.3 | 23.3 |
| 0.5 | 0.80 | 25 | 73.70 | 0.758 | 1.0515 | 1.4 | 27.9 |
| 1.0 | 0.80 | 10 | 88.20 | 0.737 | 0.9321 | 1.3 | 20.9 |
| 1.0 | 0.80 | 15 | 83.20 | 0.768 | 0.9915 | 1.3 | 22.5 |
| 1.0 | 0.80 | 20 | 78.20 | 0.768 | 1.0317 | 1.3 | 25.5 |
| 1.0 | 0.80 | 25 | 73.20 | 0.756 | 1.0838 | 1.4 | 30.2 |
| 2.0 | 0.80 | 10 | 87.20 | 0.773 | 1.0304 | 1.3 | 25.0 |

TABLE 3-continued

| Density results for batches containing 0, 0.1, 0.5, 1 and 2% (w/w) magnesium stearate | | | | | | | |
|---|---|---|---|---|---|---|---|
| Batch Details | | | | Density Results | | | |
| MgSt (% w/w) | FP (% w/w) | S400 (% w/w) | SV003 (% w/w) | Poured Density (g/ml) | Tapped Density (g/ml) | Hausner Ratio (AU) | Carrs Index (%) |
| 2.0 | 0.80 | 15 | 82.20 | 0.774 | 1.0166 | 1.3 | 23.9 |
| 2.0 | 0.80 | 20 | 77.20 | 0.765 | 1.0611 | 1.4 | 27.9 |
| 2.0 | 0.80 | 25 | 72.20 | 0.751 | 1.0572 | 1.4 | 28.9 |

TABLE 4

| Particle size analysis results for batches containing 0, 0.1, 0.5, 1 and 2% (w/w) magnesium stearate | | | | | | | |
|---|---|---|---|---|---|---|---|
| Batch Details | | | | | | | |
| MgSt | FP | S400 | SV003 | Particle Size Results | | | |
| (% w/w) | (% w/w) | (% w/w) | (% w/w) | x10 (μm) | x50 (μm) | x90 (μm) | <10 μm (%) |
| 0 | 0.80 | 10 | 89.20 | 7.22 | 56.33 | 95.32 | 12.34 |
| 0 | 0.80 | 15 | 84.20 | 4.92 | 53.35 | 93.53 | 16.51 |
| 0 | 0.80 | 20 | 79.20 | 3.92 | 50.11 | 91.44 | 20.22 |
| 0 | 0.80 | 25 | 74.20 | 3.23 | 45.79 | 89.78 | 24.47 |
| 0.1 | 0.80 | 10 | 89.10 | 6.57 | 55.07 | 92.11 | 13.16 |
| 0.1 | 0.80 | 15 | 84.10 | 4.57 | 51.90 | 90.03 | 17.59 |
| 0.1 | 0.80 | 20 | 79.10 | 3.63 | 48.51 | 89.14 | 21.61 |
| 0.1 | 0.80 | 25 | 74.10 | 3.12 | 43.73 | 86.43 | 25.64 |
| 0.5 | 0.80 | 10 | 88.70 | 7.87 | 55.97 | 93.07 | 11.73 |
| 0.5 | 0.80 | 15 | 83.70 | 5.19 | 52.98 | 91.30 | 16.16 |
| 0.5 | 0.80 | 20 | 78.70 | 3.88 | 49.88 | 89.22 | 20.46 |
| 0.5 | 0.80 | 25 | 73.70 | 3.34 | 45.72 | 86.07 | 24.00 |
| 1.0 | 0.80 | 10 | 88.20 | 8.38 | 56.42 | 92.50 | 11.25 |
| 1.0 | 0.80 | 15 | 83.20 | 5.09 | 53.56 | 93.52 | 16.17 |
| 1.0 | 0.80 | 20 | 78.20 | 3.75 | 49.86 | 91.99 | 20.88 |
| 1.0 | 0.80 | 25 | 73.20 | 3.33 | 45.34 | 89.34 | 24.39 |
| 2.0 | 0.80 | 10 | 87.20 | 6.30 | 55.86 | 95.65 | 13.36 |
| 2.0 | 0.80 | 15 | 82.20 | 3.83 | 51.90 | 92.87 | 19.15 |
| 2.0 | 0.80 | 20 | 77.20 | 2.93 | 47.58 | 89.03 | 23.95 |
| 2.0 | 0.80 | 25 | 72.20 | 2.69 | 42.91 | 86.95 | 27.59 |

Conclusions

The addition of magnesium stearate at an optimised level can be used to control or negate the influence of fine excipient particles in formulations with respect to the formulation density and flow characteristics; thus producing formulations which overcome many of the problems associated with volume based filling equipment such as changes in fill mass and dose variability caused by poor flow characteristics.

It is also proposed that the optimum level of magnesium stearate required is dependent on the quantity of fine material present in the inhaled formulation.

Example 2

Formulation blends (200 g) with and without magnesium stearate were manufactured as detailed in Table 2 with a selection of these formulations containing 2% and 5% MgSt (w/w) respectively.

TABLE 5

| Examples of formulation content percentage % w/w | | | | | |
|---|---|---|---|---|---|
| Sorbolac | | Magnesium stearate | | SV003 | |
| % | g | % | g | % | g |
| 0 | 0 | 2 | 4 | 98 | 196 |
| 15 | 30 | 2 | 4 | 83 | 166 |
| 18.5 | 37 | 2 | 4 | 79.5 | 159 |
| 25 | 50 | 2 | 4 | 73 | 146 |
| 37.5 | 75 | 2 | 4 | 60.5 | 121 |
| 50 | 100 | 2 | 4 | 48 | 96 |
| 62.5 | 125 | 2 | 4 | 35.5 | 71 |
| 75 | 150 | 2 | 4 | 23 | 46 |
| 87.5 | 175 | 2 | 4 | 10.5 | 21 |
| 0 | 0 | 5 | 10 | 95 | 190 |
| 15 | 30 | 5 | 10 | 80 | 160 |
| 18.5 | 37 | 5 | 10 | 76.5 | 153 |
| 25 | 50 | 5 | 10 | 70 | 140 |
| 37.5 | 75 | 5 | 10 | 57.5 | 115 |
| 50 | 100 | 5 | 10 | 45 | 90 |
| 62.5 | 125 | 5 | 10 | 32.5 | 65 |
| 75 | 150 | 5 | 10 | 20 | 40 |
| 87.5 | 175 | 5 | 10 | 7.5 | 15 |
| 100 | 200 | 0 | 0 | 0 | 0 |

Respitose SV003 (supplied by DFE Pharma) was used as the coarse fraction and this was particle sized before blending. Respitose SV003 was sieved using a seize shaker (e.g. Russel Finex) to produce a 45-63 μm sieved fraction. This was a two stage process using a 45 μm sieve to remove the <45 μm material. The material that did not pass the sieve was retained and passed through a 63 μm sieve. The sieved fraction that was retained was used as the coarse lactose for the placebo formulations. A particle size determination was made of the sieved fraction with the results recorded.

Sorbolac 400 (supplied by Meggle) was used as the fine fraction and a particle size determination was made before blending with the results recorded.

Magnesium Stearate (supplied by Peter Greven) was used as a force control agent and a particle size determination was made before blending with the results recorded. The Magnesium Stearate was added at amounts of 2% and 5% w/w.

Fluticasone Propionate (supplied by Sterling) was used as the active pharmaceutical ingredient. A particle size determination was made before blending with the results recorded.

TABLE 6

| Blend compositions Formulation Constituents (% w/w) | | | |
|---|---|---|---|
| Magnesium Stearate | Fluticasone Propionate | S400 | SV003 |
| 0 | 0.8 | 10 | 89.20 |
| 0 | 0.8 | 15 | 84.20 |
| 0 | 0.8 | 20 | 79.20 |
| 0 | 0.8 | 25 | 74.20 |
| 0.5 | 0.8 | 10 | 88.70 |
| 0.5 | 0.8 | 15 | 83.70 |
| 0.5 | 0.8 | 20 | 78.70 |
| 0.5 | 0.8 | 25 | 73.70 |
| 1 | 0.8 | 10 | 88.20 |
| 1 | 0.8 | 15 | 83.20 |
| 1 | 0.8 | 20 | 78.20 |
| 1 | 0.8 | 25 | 73.20 |
| 2 | 0.8 | 10 | 87.20 |
| 2 | 0.8 | 15 | 82.20 |
| 2 | 0.8 | 20 | 77.20 |
| 2 | 0.8 | 25 | 72.20 |

TABLE 6-continued

| Blend compositions Formulation Constituents (% w/w) | | | |
|---|---|---|---|
| Magnesium Stearate | Fluticasone Propionate | S400 | SV003 |
| 0 | 2.4 | 30 | 267.6 |
| 0 | 2.4 | 45 | 252.6 |
| 0 | 2.4 | 60 | 237.6 |
| 0 | 2.4 | 75 | 222.6 |
| 1.5 | 2.4 | 30 | 266.1 |
| 1.5 | 2.4 | 45 | 251.1 |
| 1.5 | 2.4 | 60 | 236.1 |
| 1.5 | 2.4 | 75 | 221.1 |
| 3 | 2.4 | 30 | 264.6 |
| 3 | 2.4 | 45 | 249.6 |
| 3 | 2.4 | 60 | 234.6 |
| 3 | 2.4 | 75 | 219.6 |
| 6 | 2.4 | 30 | 261.6 |
| 6 | 2.4 | 45 | 246.6 |
| 6 | 2.4 | 60 | 231.6 |
| 6 | 2.4 | 75 | 216.6 |

The formulations were manufactured to a 300 g scale in the amounts outlined in Table 2 (above) using a Comil and a Diosna P1/6.

Firstly, the fluticasone propionate was sieved the using a 500 μm sieve.

Half of the SV003 fraction was Comiled, followed sequentially by the magnesium stearate, fluticasone propionate, Sorbolac 40000 and the remaining SV003 at 1000 rpm using a Comil 457 μm screen.

This comiled material was transferred to a 1 liter Diosna bowl and blended at rpm for 7 min 48 sec. The blending was processed with a blanking plate instead of the chopper.

The blended material was removed for storage in sealed glass amber jars at ambient laboratory conditions. Each Blend was tested for content uniformity An Omnidose automated powder filling apparatus (HarroHöfliger) was set up for filling unit doses using a 16 $mm^3$ blister format dosing drum and standard equipment settings.

The Omnidose automated powder filling apparatus hopper was charged with each formulation in turn and a dose weight evaluation was carried using a 5 figure analytical balance. The results are reported in FIG. 1.

Conclusions

Physical characterisation and comparison to similar blends without magnesium stearate yielded the following observations. The blends containing magnesium stearate exhibited generally higher bulk density measurements which were largely independent of the change in fine particle content until relatively high concentrations of S400. The effect was more pronounced at the 2% w/w magnesium stearate level. The blends containing magnesium stearate exhibited generally higher tapped density measurements which increased with the increase in fine particle content until relatively high concentrations of S400. This was compared to a general downward trend in tapped density with increased fine particle content for comparable non-magnesium stearate blends. The effect was more pronounced at the 2% w/w magnesium stearate level. A significant reduction in flow energy which follows a more linear relationship compared to non-magnesium stearate blends.

It is proposed that the addition of magnesium stearate at an optimised level could be used to control or negate the influence of variable fine particle lactose and/or API content in formulations with respect to the formulation density and flow characteristics; thus producing formulations which overcome many of the inherent problems associated with volume based filling equipment such as changes in fill mass and dose variability caused by poor flow characteristics.

It is also proposed that the optimum level of magnesium stearate required is dependent on the particle size distribution of the carrier.

Example 3

The 3Pi dosator is a volumetric filling system which utilises a tube to collect and transfer a pre-determined volume of powder from a powder reservoir into a blister or capsule.

Within the filling tube is a piston which can be used to apply an amount of compression to the formulation. If the correct level of compression is applied, dose cohesion and dose weight uniformity is improved. If however, dose compression is applied incorrectly, the compression can cause hard unaerosolisable doses that reside in the blister or capsule.

Blend Manufacture

Coarse Fraction: Lactohale LH200 (supplied by Domo) was used as the coarse fraction and was particle sized according to before blending.

Fine Fraction: Sorboiac 400 (supplied by Meggle) was used as the fine fraction and was particle sized before blending.

Magnesium Stearate: Magnesium stearate (supplied by Peter Greven) was used to assist dispensed inhalable dose disaggregation.

Fluticasone Propionate (FP): Fluticasone Propionate (supplied by Sterling) was used as the active pharmaceutical ingredient and was particle sized before blending.

Formulation Component Particle Size

Particle size data of the formulation components was established prior to manufacture.

TABLE 7

| The particle size data of the formulation components. | | | |
|---|---|---|---|
| | D10 (μm) | D50 (μm) | D90 (μm) |
| Lactohale LH200 | 9.66 | 71.44 | 144.82 |
| Sorbolac S400 | 1.91 | 8.41 | 19.37 |
| Magnesium Stearate | 3.01 | 9.08 | 26.23 |
| Fluticasone Propionate | 0.92 | 2.06 | 4.07 |

Blending Procedure

The formulations were manufactured to 300 g scale in the ratio described in Table 8 below. The fluticasone propionate was sieved using a 500 μm sieve. Half the LH200 was processed using a Comil at 1000 rpm using a 457 μm screen, followed by the magnesium stearate, then followed by the fluticasone propionate, then the Sorbolac 400 and finally with the remaining LH200 all at the Comil conditions mentioned above. This processed material was transferred into a 1 liter Diosna bowl and blended at 1457 rpm for 8 mins. This blended material was removed for storage in sealed glass amber jars at ambient laboratory conditions.

TABLE 8

| Composition of the manufactured formulations Formulation Constituents (% w/w) | | | |
|---|---|---|---|
| Magnesium Stearate | Fluticasone Propionate | Fine fraction (S400) | Coarse fraction (LH200) |
| 0.0 | 0.8 | 10 | 89.2 |
| 0.0 | 0.8 | 20 | 79.2 |
| 0.0 | 0.8 | 30 | 69.2 |
| 0.5 | 0.8 | 10 | 88.7 |
| 0.5 | 0.8 | 20 | 78.7 |
| 0.5 | 0.8 | 30 | 68.7 |
| 2.0 | 0.8 | 10 | 87.2 |
| 2.0 | 0.8 | 20 | 77.2 |
| 2.0 | 0.8 | 30 | 67.2 |

Content Uniformity

Each blend was tested for content uniformity.

TABLE 9

Composition of the manufactured formulations and blend uniformity data for blends comprising 0.0, 0.5 and 2.0% (w/w) magnesium stearate.

| Formulation Constituents (% w/w) | | | | Content Uniformity | | |
|---|---|---|---|---|---|---|
| | | | | Mean | % | |
| MgSt | FP | S400 | LH200 | (% w/w) | Theory | RSD % |
| 0.0 | 0.8 | 10 | 89.2 | 0.754 | 94.20 | 1.6 |
| 0.0 | 0.8 | 20 | 79.2 | 0.777 | 97.10 | 1.7 |
| 0.0 | 0.8 | 30 | 69.2 | 0.767 | 95.88 | 1.0 |
| 0.5 | 0.8 | 10 | 88.7 | 0.730 | 91.22 | 1.9 |
| 0.5 | 0.8 | 20 | 78.7 | 0.763 | 95.41 | 3.1 |
| 0.5 | 0.8 | 30 | 68.7 | 0.753 | 94.16 | 3.5 |
| 2.0 | 0.8 | 10 | 87.2 | 0.775 | 96.91 | 1.8 |
| 2.0 | 0.8 | 20 | 77.2 | 0.782 | 97.77 | 1.1 |
| 2.0 | 0.8 | 30 | 67.2 | 0.767 | 95.89 | 1.9 |

Blend Particle Size Analysis

The particle size distribution of each blend was tested.

TABLE 10

Composition of the manufactured formulations and particle size distribution analysis data for blends comprising 0.0, 0.5 and 2.0% (w/w) magnesium stearate.

| Formulation Constituents (% w/w) | | | | Particle Size | | |
|---|---|---|---|---|---|---|
| | | | | D10 | D50 | D90 |
| MgSt | FP | S400 | LH200 | (μm) | (μm) | (μm) |
| 0.0 | 0.8 | 10 | 89.2 | 8.18 | 92.41 | 154.27 |
| 0.0 | 0.8 | 20 | 79.2 | 3.79 | 79.37 | 146.09 |
| 0.0 | 0.8 | 30 | 69.2 | 2.84 | 62.86 | 141.77 |
| 0.5 | 0.8 | 10 | 88.7 | 7.81 | 92.33 | 153.78 |
| 0.5 | 0.8 | 20 | 78.7 | 3.45 | 80.30 | 147.35 |
| 0.5 | 0.8 | 30 | 68.7 | 2.68 | 65.25 | 143.29 |
| 2.0 | 0.8 | 10 | 87.2 | 5.42 | 89.81 | 152.75 |
| 2.0 | 0.8 | 20 | 77.2 | 2.53 | 76.49 | 148.54 |
| 2.0 | 0.8 | 30 | 67.2 | 2.09 | 53.17 | 141.55 |

Dosator Setup, Sample Compression Evaluation

The 3Pi Dosator was set up for each experimental run. The hopper was charged with formulation and a dose weight evaluation was carried out using a 5 figure analytical balance. Blister samples were sealed using a bench top blister sealer.

The process was as follows:

1. 25 doses to waste, then
2. 20 weight samples (Run 1), then
3. 10 inhaler blisters filled and sealed with their individual weights recorded.

Blister shot weights were evaluated in an inhaler device for each set of filling parameters by DUSA using a 4 figure analytical balance as detailed below:

Flow rate: 60 Limin

Shot time: 2 Seconds

Replicates: 10

Results are presented in FIG. 5 and FIG. 6

Conclusions

The data presented in FIG. 5 for the 0% (w/w) magnesium stearate blends shows an unacceptable blister evacuation with a high degree of variability for both 10% and 30% S40000 formulations.

The data presented in FIG. 5 for the 0.5% (w/w) magnesium stearate blends shows that the variability has decreases for the 10% S40000 formulation and acceptable evacuation for the 30% S40000 formulation.

The data presented in FIG. 5 for the 2.0% (w/w) magnesium stearate blends shows consistent evacuation for both the 10% S40000 formulation and the 30% S400 formulation.

FIG. 6 shows a decrease in dose weight variability from 0% magnesium stearate to 0.5% magnesium stearate indicating that 0.5% magnesium stearate assists in maintaining reproducible doses. As the concentration of magnesium stearate is further increased to 2.0%, the dose reproducibility is maintained with the exception of two doses that failed to leave the dosator pin (30% S400 formulation). This is thought to be due to the powder plugs adhering and being pulled back into the pin, an affect known as Capping. This thought to be as a result of the highly cohesive nature of the formulation.

The use of magnesium stearate as a flow aid to assist in dispensed inhalable dose disaggregation is disclosed. This new use dramatically improves capability of the dosator filling apparatus to dispense accurate, reproducible and unaerosolisable doses.

Example 4

A variety of formulations comprising either Respitose SV003, Respitose ML001 or Lactohale LH200 as a representative excipient carrier system, with either 0%, 0.1%, 0.5% or 1.0% (w/w) magnesium stearate with varying amounts of added model fine particle component (S400) were manufactured and dosed from a Harro Höfliger Omnidose automated powder filling apparatus.

Blend Manufacture

The various formulations comprised the following constituent parts:

Coarse Fraction: either Respitose SV003, Lactohale LH200 (already containing 14% (w/w) fines) and Respitose ML001 were used as coarse fractions and were subject to particle size analysis before blending (Table 11).

Fine Cohesive Fraction: Sorbolac S400 was used as the model fine fraction component and was subject to particle size analysis before blending (Table 11).

Stearate: Magnesium stearate (supplied by Peter Greven) was used as a force control agent and a particle size determination was made before blending with the results recorded (Table 11).

Model Drug: Fluticasone propionate (FP) (supplied by Sterling) was used as the active pharmaceutical ingredient and a particle size determination was made before blending with the results recorded (Table 11).

Formulation Component PSD

Particle size data of the formulation components was established prior to manufacture.

TABLE 11

The particle size data of the formulation components.

| | $D_{10}$ (μm) | $D_{50}$ (μm) | $D_{90}$ (μm) | % <10 μm |
|---|---|---|---|---|
| Respitose SV003 | 32.01 | 58.61 | 91.84 | 3.83 |
| Respitose ML001 | 4.57 | 47.59 | 140.88 | 17.10 |
| Lactohale LH200 | 9.66 | 71.44 | 144.82 | 10.28 |
| Sorbolac S400 | 1.53 | 7.77 | 18.76 | 61.74 |
| Magnesium Stearate | 1.44 | 5.56 | 18.11 | 76.44 |
| Fluticasone Propionate | 0.9 | 2.10 | 4.20 | 100 |

Blending Procedure

The formulations were manufactured to 300 g scale in the ratios described in Tables 12, 13 and 14. The fluticasone propionate was sieved using a 500 μm sieve. Half the coarse lactose was processed using a Comil at 1000 rpm using a 457 μm screen, followed by the magnesium stearate (where applicable), then followed by the fluticasone propionate, then the Sorbolac 400 (where applicable), and finally with the remaining coarse lactose all at the Comil conditions mentioned above. This processed material was transferred into a 1 liter Diosna bowl and blended at 1457 rpm for 8 mins. This blended material was removed for storage in sealed glass amber jars at ambient laboratory conditions.

Analysis Procedure

Using an FT4 Powder Rheometer (Freeman Technology) a sample of each manufactured blend was subjected to the following tests as described in the FT4 user manual and/or associated Freeman Technology literature.

The FT4 Aeration test determines Basic Flowability Energy, Specific Energy, Conditioned Bulk Density, Aerated Energy, Aeration Ratio and Normalised Aeration Sensitivity. The standard 25 mm Aeration program was optimised to achieve improved reproducibility over the Freeman method.

The FT4 Permeability test determines the Pressure Drop at compaction pressures from 0.6 kPa to 15 kPa. The standard 25 mm Permeability program was optimised to achieve improved reproducibility over the Freeman method.

The FT4 Shear test was performed using the standard 25 mm Shear 3 kPa program which determines incipient shear stress up to a compaction pressure of kPa.

The FT4 Compressibility test was performed using the standard 25 mm Compressibility 1-15 kPa which determines percentage compressibility up to a compaction pressure of 15 kPa.

Blend Particle PSD

The particle size distribution of each blend was tested and expressed as $D_{10}$, $D_{50}$, $D_{90}$ and %<10 μm. All blends and lactose were measured dry at a dispersion pressure of 2 bar.

TABLE 12

Composition of the manufactured formulations (300 g) and particle size distribution analysis data for blends comprising LH200, S400 fines and 0.0, 0.1, 0.5 and 1.0% (w/w) magnesium stearate.

| Blend Constituents (% w/w) | | | | Blend Particle Size Distribution | | | |
|---|---|---|---|---|---|---|---|
| MgSt | FP | S400 | LH200 (14% fines) | $D_{10}$ (μm) | $D_{50}$ (μm) | $D_{90}$ (μm) | % < 10 μm |
| 0.0 | 0.8 | 5 | 94.2 | 6.25 | 65.36 | 141.76 | 14.21 |
| 0.1 | 0.8 | 5 | 94.1 | 5.92 | 65.31 | 142.16 | 14.75 |
| 0.5 | 0.8 | 5 | 93.7 | 5.96 | 65.81 | 142.31 | 14.55 |
| 1 | 0.8 | 5 | 93.2 | 5.13 | 64.25 | 142.15 | 15.82 |
| 0.0 | 0.8 | 20 | 79.2 | 3.30 | 38.87 | 134.16 | 25.79 |
| 0.1 | 0.8 | 20 | 79.1 | 3.24 | 41.35 | 134.96 | 25.21 |
| 0.5 | 0.8 | 20 | 78.7 | 3.05 | 39.92 | 134.58 | 26.06 |
| 1 | 0.8 | 20 | 78.2 | 2.89 | 37.29 | 133.95 | 27.11 |

TABLE 13

Composition of the manufactured formulations (300 g) and particle size distribution analysis data for blends comprising ML001, S400 and 0.0, 0.1, 0.5 and 1.0% (w/w) magnesium stearate.

| Blend Constituents (% w/w) | | | | Blend Particle Size Distribution | | | |
|---|---|---|---|---|---|---|---|
| MgSt | FP | S400 | ML001 | $D_{10}$ (μm) | $D_{50}$ (μm) | $D_{90}$ (μm) | % < 10 μm |
| 0.0 | 0.8 | 0 | 99.2 | 3.66 | 46.69 | 141.44 | 18.59 |
| 0.1 | 0.8 | 0 | 99.1 | 3.65 | 46.36 | 140.31 | 18.62 |
| 0.5 | 0.8 | 0 | 98.7 | 3.54 | 46.70 | 142.21 | 18.90 |
| 1 | 0.8 | 0 | 98.2 | 3.11 | 44.89 | 139.95 | 20.20 |
| 0.0 | 0.8 | 2 | 97.2 | 3.47 | 45.15 | 139.69 | 19.66 |
| 0.1 | 0.8 | 2 | 97.1 | 3.48 | 44.77 | 139.80 | 19.72 |
| 0.5 | 0.8 | 2 | 96.7 | 3.27 | 44.58 | 140.99 | 20.36 |
| 1 | 0.8 | 2 | 96.2 | 2.99 | 42.72 | 138.57 | 21.36 |
| 0.0 | 0.8 | 12 | 87.2 | 2.80 | 33.10 | 130.76 | 26.15 |
| 0.1 | 0.8 | 12 | 87.1 | 2.83 | 33.99 | 131.80 | 25.70 |
| 0.5 | 0.8 | 12 | 86.7 | 2.65 | 33.06 | 132.33 | 26.65 |
| 1 | 0.8 | 12 | 86.2 | 2.56 | 32.31 | 131.42 | 27.29 |

TABLE 14

Composition of the manufactured formulations and particle size distribution analysis data for blends comprising SV003, S400 and 0.0, 0.1, 0.5 and 1.0% (w/w) magnesium stearate.

| Blend Constituents (% w/w) | | | | Blend Particle Size Distribution | | | |
|---|---|---|---|---|---|---|---|
| MgSt | FP | S400 | SV003 | $D_{10}$ (μm) | $D_{50}$ (μm) | $D_{90}$ (μm) | % < 10 μm |
| 0.0 | 0.8 | 5 | 94.2 | 14.86 | 56.94 | 91.08 | 8.04 |
| 0.1 | 0.8 | 5 | 94.1 | 15.42 | 56.90 | 90.95 | 7.87 |
| 0.5 | 0.8 | 5 | 93.7 | 13.45 | 56.45 | 90.54 | 8.52 |
| 1 | 0.8 | 5 | 93.2 | 13.41 | 56.64 | 90.85 | 8.53 |
| 0.0 | 0.8 | 20 | 79.2 | 3.80 | 47.73 | 85.60 | 21.18 |
| 0.1 | 0.8 | 20 | 79.1 | 3.91 | 48.03 | 85.56 | 20.64 |
| 0.5 | 0.8 | 20 | 78.7 | 3.56 | 47.47 | 85.41 | 21.53 |
| 1 | 0.8 | 20 | 78.2 | 3.32 | 47.01 | 85.40 | 22.50 |

Compared with the constituent carrier PSDs, the blend PSDs shifted to the smaller size for those blends that contained increased levels of S400, and also for those blends that contained increased levels of magnesium stearate, although the change with magnesium stearate was negligible.

The LH2000 and ML001 blends have broad size distributions due to their milled method of manufacture. The ML001 blends have the greatest concentration of fine particles and are likely to be the most cohesive. In contrast, SV003 blends have a much narrower distribution because it is a sieved excipient carrier with a narrower size distribution.

Harro Höfliger Omnidose Filling

The Harro Höfliger Omnidose automated powder filling apparatus was set up for filling unit doses using a standard 15 $mm^3$ dosing drum and standard equipment settings.

The hopper was filled with formulation and a dose weight evaluation was carried out as follows using a 5 figure analytical balance:

1. 50 doses to waste
2. 24 weight samples (Run 1)
3. 100 dosing cycles to waste (equivalent to 400 individual doses)
4. 24 weight samples (Run 2)
5. 100 dosing cycles to waste (equivalent to 400 individual doses)
6. 24 weight samples (Run 3)
7. 100 dosing cycles to waste (equivalent to 400 individual doses)
8. 24 weight samples (Run 4)
9. 100 dosing cycles to waste (equivalent to 400 individual doses)
10. 24 weight samples (Run 5)

Acceptance Criteria

The fill weight data and observations were evaluated in terms of dose weight reproducibility and equipment failure modes. The target fill weight was derived for each lactose grade as the mean fill weight obtained from the lowest percentage S400 content formulation which contained no magnesium stearate.

Acceptance limits were based on ±10% of the mean weight. Individual weights falling outside of this range were deemed unacceptable. Common modes of failure are caused by poor powder flow within the hopper and evident in the fill weight variability As a volumetric system the weight of the fixed volume dispensed dose is directly proportional to the formulation density, therefore changes in density have a direct impact on dispensed weight under common dosing conditions.

Conclusions

This example produced a range of formulations to challenge the failure point of a drum filling apparatus in terms of dispensed dose reproducibility i.e. the amount of total powder dispensed from the drum filler into a capsule or blister. This example demonstrates that the powder filling performance using a drum filling apparatus (e.g. Harro Höfliger Omnidose filling machine) varied with respect to excipient type and that the dose reproducibility failure point was observed at varying fine particle contents depending on the lactose carrier used.

The fill weight reproducibility failure is a function of the total fine particle content causing poor powder flow in the drum filling apparatus' hopper, leading to partial dosing. Some excipient carrier systems have higher levels of inherent fines (e.g. ML001) contributing to poor powder flow and poorly reproducible dosing.

Blends were manufactured with a range of lactose carriers with different levels of inherent and added fines, with and without a stearate, in this case magnesium stearate. The addition of magnesium stearate to poorly performing formulations improves filling characteristics of inhalable formulations, in particular dispensed dose reproducibility.

The invention claimed is:

1. A method of improving dispensed dosing reproducibility of an inhalable pharmaceutical formulation comprising greater than 10% (w/w) fines from an automated powder filling apparatus, comprising submitting the inhalable pharmaceutical formulation to compression and shearing forces in the presence of magnesium stearate, wherein the inhalable formulation comprises a pharmaceutically active material selected from budesonide, formoterol fumarate, glycopyrronium bromide, indacaterol maleate, umeclidinium bromide, vilanterol trifenatate, tiotropium bromide, salmeterol xinafoate or fluticasone propionate, wherein the magnesium stearate has a $D_{10}≤3$ μm, $D_{50}≤10$ μm and $D_{90}≤30$ μm as determined by laser diffraction particle size analysis, and wherein the magnesium stearate is present in an amount of from 0.1% to 50% by weight of the inhalable pharmaceutical formulation.

2. The method of claim 1, wherein the inhalable pharmaceutical formulation further comprises one or more stearate selected from the group consisting of calcium stearate and sodium stearate.

3. The method of claim 1, wherein the magnesium stearate has a $D_{10}≤2$ μm, $D_{50}≤6$ μm and $D_{90}≤20$ μm as determined by laser diffraction particle size analysis.

4. The method of claim 1, wherein the inhalable formulation has a fines content in an amount greater than 10% by mass of the formulation as determined by laser diffraction particle size analysis.

5. The method of claim 1, wherein the inhalable formulation further comprises carrier particles, with a $D_{50}$ greater than 45 μm as determined by laser diffraction particle size analysis.

* * * * *